(12) United States Patent
Kaumaya

(10) Patent No.: US 7,691,396 B2
(45) Date of Patent: Apr. 6, 2010

(54) CHIMERIC PEPTIDES COMPRISING HER-2 B-CELL EPITOPES AND MEASLES VIRUS FUSION PROTEIN T-CELL EPITOPES

(75) Inventor: Pravin Kaumaya, Westerville, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 157 days.

(21) Appl. No.: 11/424,526

(22) Filed: Jun. 15, 2006

(65) Prior Publication Data

US 2007/0060516 A1    Mar. 15, 2007

Related U.S. Application Data

(60) Provisional application No. 60/690,574, filed on Jun. 15, 2005.

(51) Int. Cl.
*A61K 39/00* (2006.01)

(52) U.S. Cl. ............. 424/277.1; 424/185.1; 424/192.1; 424/194.1; 530/300; 514/2

(58) Field of Classification Search ................. None
See application file for complete search history.

(56) References Cited

OTHER PUBLICATIONS

Dakappagari et al, J of Immunology, 2003, 170:4242-4253.*
Stedman's Medical Dictionary, p. 1.*
GenBank Accession No. PO4626 (NCBI, p. 1-23).*
Dakappagari et al II (Cancer Research, 2000, 60:3782-3789).*
Dakappagari et al (Cancer Research, 2000, 60:3782-3789).*

* cited by examiner

*Primary Examiner*—Laura B Goddard
(74) *Attorney, Agent, or Firm*—Calfee, Halter & Griswold LLP

(57) ABSTRACT

Compositions, methods, and vaccines that may stimulate the immune system and that may be used for treating malignancies associated with overexpression of the HER-2 protein are provided. Such compositions include epitopes of the HER-2 proteins.

12 Claims, 20 Drawing Sheets

```
   1  melaalcrwg lllallppga astqvctgtd mklrlpaspe thldmlrhly qgcqvvqgnl
  61  eltylptnas lsflqdiqev qgyvliahnq vrqvplqrlr ivrgtqlfed nyalavldng
 121  dplnnttpvt gaspgglrel qlrslteilk ggvliqrnpq lcyqdtilwk difhknnqla
 181  ltlidtnrsr achpcspmck gsrcwgesse dcqsltrtvc aggcarckgp lptdccheqc
 241  aagctgpkhs dclaclhfnh sgicelhcpa lvtyntdtfe smpnpegryt fgascvtacp
 301  ynylstdvgs ctlvcplhnq evtaedgtqr cekcskpcar vcyglgmehl revravtsan
 361  iqefagckki fgslaflpes fdgdpasnta plqpeqlqvf etleeitgyl yisawpdslp
 421  dlsvfqnlqv irgrilhnga ysltlqglgi swlglrslre lgsglalihh nthlcfvhtv
 481  pwdqlfrnph qallhtanrp edecvgegla chqlcarghc wgpgptqcvn csqflrgqec
 541  veecrvlqgl preyvnarhc lpchpecqpq ngsvtcfgpe adqcvacahy kdppfcvarc
 601  psgvkpdlsy mpiwkfpdee gacqpcpinc thscvdlddk gcpaeqrasp ltsivsavvg
 661  illvvvlgvv fgilikrrqq kirkytmrrl lqetelvepl tpsgampnqa qmrilketel
 721  rkvkvlgsga fgtvykgiwi pdgenvkipv aikvlrents pkankeilde ayvmagvgsp
 781  yvsrllgicl tstvqlvtql mpygclldhv renrgrlgsq dllnwcmqia kgmsyledvr
 841  lvhrdlaarn vlvkspnhvk itdfglarll dideteyhad ggkvpikwma lesilrrrft
 901  hqsdvwsygv tvwelmtfga kpydgipare ipdllekger lpqppictid vymimvkcwm
 961  idsecrprfr elvsefsrma rdpqrfvviq nedlgpaspl dstfyrslle dddmgdlvda
1021  eeylvpqqgf fcpdpapgag gmvhhrhrss strsgggdlt lglepseeea prsplapseg
1081  agsdvfdgdl gmgaakglqs lpthdpsplq rysedptvpl psetdgyvap ltcspqpeyv
1141  nqpdvrpqpp spregplpaa rpagatlera ktlspgkngv vkdvfafgga venpeyltpq
1201  ggaapqphpp pafspafdnl yywdqdpper gappstfkgt ptaenpeylg ldvpv
```

FIGURE 1

A
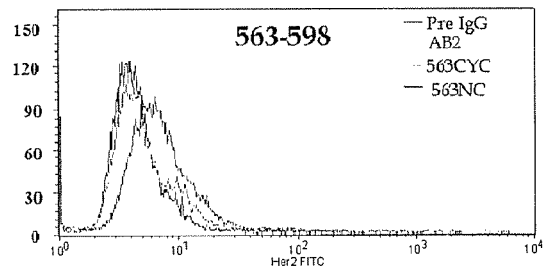
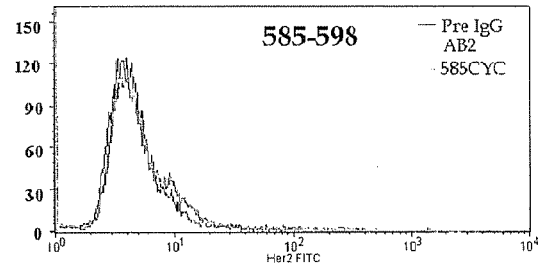
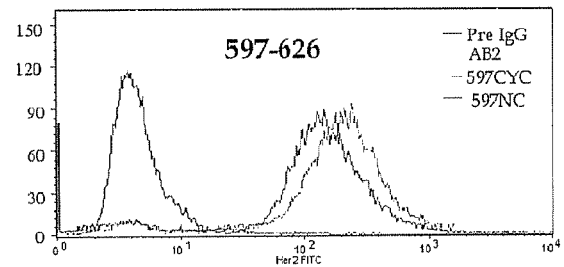
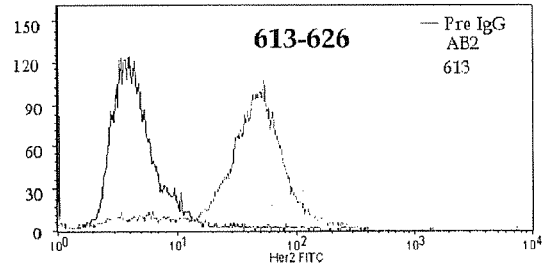
B
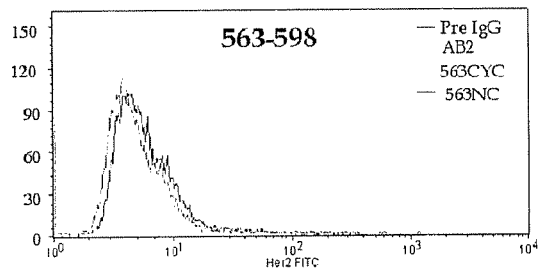
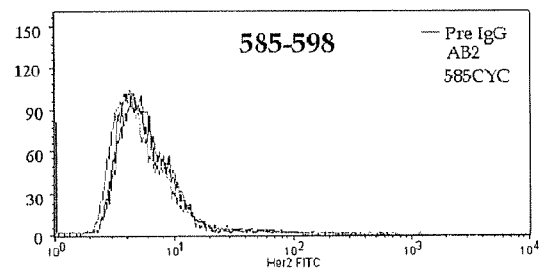
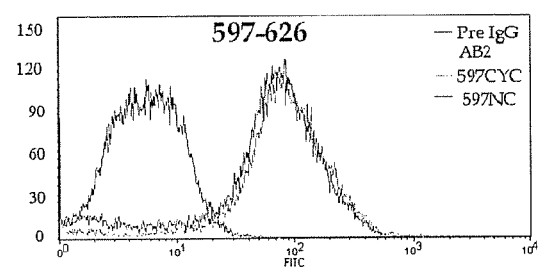
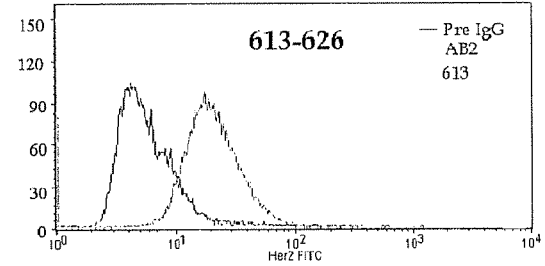
FIGURE 13

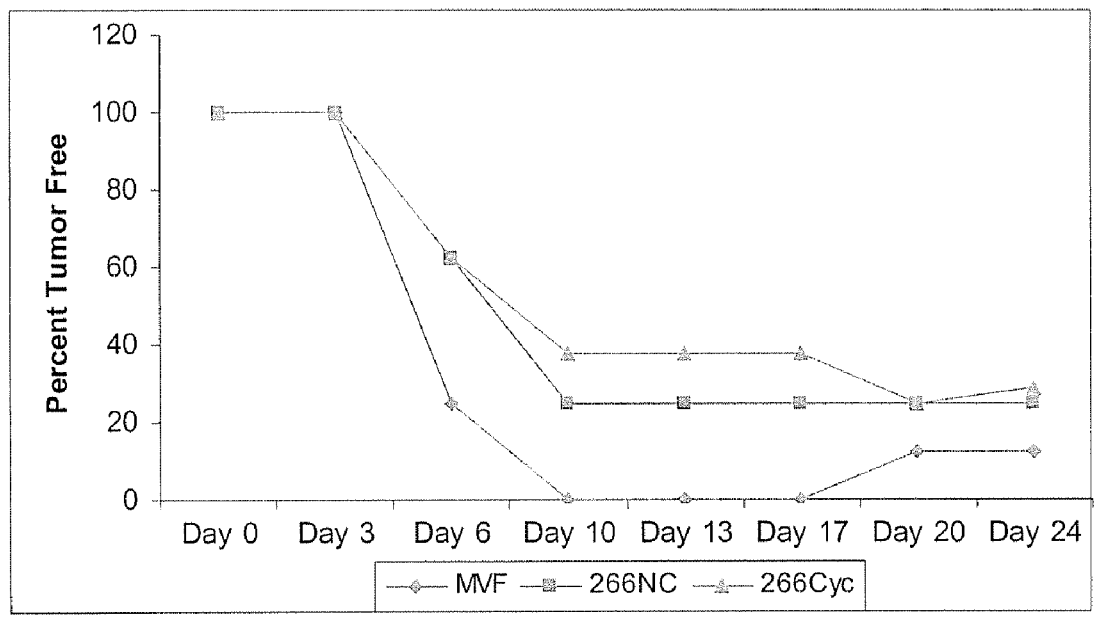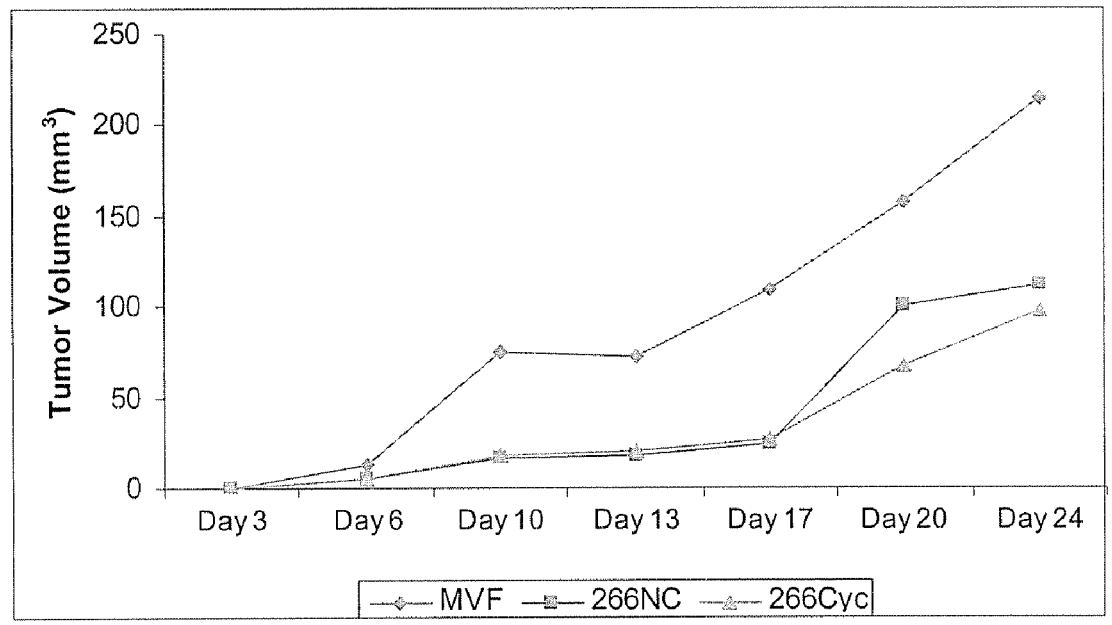
FIGURE 30

CHIMERIC PEPTIDES COMPRISING HER-2 B-CELL EPITOPES AND MEASLES VIRUS FUSION PROTEIN T-CELL EPITOPES

CROSS-REFERENCE TO RELATED APPLICATION

This application claims priority to and any other benefit of U.S. Provisional Application No. 60/690,574, filed Jun. 15, 2005, entitled HER-2 Peptides, the entirety of which is herein incorporated by reference.

GOVERNMENT SUPPORT

The work described in this application was supported, at least in part, by grants NIH 5ROI CA 84356 from the National Institute of Health. The United States government has certain rights in this invention.

BACKGROUND

Currently, the most common approaches to treating breast cancer involve surgery, chemical intervention, and/or radiotherapy. Unless the cancer is restricted to a defined area, surgery alone cannot eliminate the cancer. Accordingly, radiation treatment is often given after surgery to destroy cancer cells that are near the surgical site and that have evaded surgery. The side effects of such treatment include skin sensitivity or itchiness, interference with the immune system, sometimes queasiness and, rarely, radiation fibrosis where an affected portion of the lung becomes fibrous. Chemotherapy may also be employed following surgery. Chemotherapy utilizes drugs that are toxic to cancer cells. Since this is not a perfectly selective system, normal cells are affected as well. Negative side effects include nausea, tiredness, loss of appetite, hair loss and diarrhea.

In view of such present therapies, attempts have been made to find additional approaches for treating breast cancer. One such approach is immunotherapy. One of the targets for an immunotherapeutic approach is the HER-2 protein. The HER-2 protein, a product of the HER-2 oncogene, is overexpressed in a variety of cancers. It is found in 50%-60% of ductal in situ carcinoma and 20%-40% of all breast cancers, as well as a substantial fraction of adenocarcinomas arising in the ovaries, prostate, colon and lung. Overexpression of the HER-2 protein is related to malignant transformation in humans. Overexpression of the HER-2 protein is also intimately associated with the aggressiveness of the malignancy, being found in one-fourth of all invasive breast cancers. Overexpression of HER-2 protein is correlated with a poor prognosis in both breast and ovarian cancer.

In recent studies, antibodies directed against the extracellular binding domain (ECD) of HER-2 have been shown to confer inhibitory effects on tumor growth in vitro and in animal models (Hudziak, R. M., et al., Mol. Cell. Biol., 9:11-65-72, 1989; Tagliabue, E., et al., Int. J. Cancer 47:933-7, 1991; Drebin, J. A., et al., Proc. Natil. Acad. Scie. USA 83:9129-33, 1986; Drebin, J. A., et al., Oncogene, 2:273-7, 1988; Drebin, J. A., et al., Oncogene, 2:387-94, 1988; and Katsumata, M., et al., Nat. Med. 1:644-8. 1995.) In addition, Phase II and III clinical trials of a recombinant humanized anti-HER-2 monoclonal antibody, Trastuzumab, in patients with metastatic, HER-2-overexpressing breast cancers produced an overall response rate of 15% as a single agent. Trastuzumab has also been shown to improve survival when combined with cytotoxic chemotherapeutics (Baselga, J., et al., J. Clin. Oncol. 14:737-44, 1996; Pegram, M. D., et al., J. Clin. Oncol., 16:2659-71, 1988.). A number of vaccine approaches targeting a recombinant HER-2 protein, the HER-2 ECD, or the ECD of rat neu, which is the rat homolog of HER-2 have also been evaluated. For example, strain NFS mice immunized with a *vaccinia* virus recombinant that expresses the ECD rat neu developed a protective antibody response against subsequent challenge with neu-transformed NIH 3T3 cells (Bernards, R., et al., Proc. Natl. Acad. Sci. USA, 84:6854-8, 1987.). Immunization of BDIX rats with the same immunogen, however, did not result in antibody response nor did it inhibit the growth of syngeneic neu-expressing B104 neuroblastoma cells, suggesting that this strategy was insufficient to induce immune responses in the rat. A polysaccharide-oncoprotein complex vaccine, consisting of the 147 amino-terminal amino acids of HER-2 ECD complexed with cholesteryl group-bearing mannan and pullulan, induced cellular and humoral immune responses that mediated rejection of HER-2-expressing sarcomas in BALB/c mice (Gu, X. G., et al., Cancer Res., 58: 3385-90, 1998.). Partial protection was shown in rat neu transgenic mice destined to develop mammary tumors by immunizing with either a purified rat neu ECD (Esserman, L. J., Cancer Immunol. Immunother., 47:337-42, 1999.) or neu-transfected allogeneic mouse fibroblasts (Cefai, D., et al., Int. J. Cancer, 83:393-400, 1999.)

Despite the results of the studies described above, it is still uncertain whether effective immune responses can be generated in humans using cell-or protein-based vaccine strategies targeting HER-2 or the HER-2 ECD, as HER-2 is a non-mutated, "self" antigen. Accordingly, it is desirable to have additional immunotherapeutic approaches for treating or preventing breast cancer and other malignancies with which overexpression of the HER-2 protein is associated.

SUMMARY

In accordance with embodiments, HER-2 B epitopes are provided. The Epitopes have a sequence of CHPEC-QPQNGSVTCFGPEADQCVACAHYKDPPFCVA (SEQ ID NO: 2); VACAHYKDPPFCVA (SEQ ID NO: 3); VARCPSGVKPDLSYMPIWKFPDEEGACQPL (SEQ ID NO: 4); IWIKFPDEEGACQPL (SEQ ID NO: 5); LHCPALV-TYNTDTFESMPNPEGRYTFGASCV (SEQ ID NO: 6); ACPYNYLSTDVGSCTLVCPLHNQEVTAEDGTQRCEK (SEQ ID NO: 7); CPLHNQEVTAEDGTQRCEK (SEQ ID NO: 8); or CPINCTHSCVDLDDKGCPAEQRAS (SEQ ID NO: 9).

Additional embodiments of the invention are described in more detail herein.

BRIEF DESCRIPTION OF THE SEVERAL VIEWS OF THE DRAWINGS

The following detailed description of embodiments of the present invention can be best understood when read in conjunction with the following drawings, where like structure is indicated with like reference numerals and in which:

FIG. 1 illustrates the HER-2 protein sequence (SEQ ID NO: 1);

FIG. 13 shows the cross-reactivity of peptide antibodies to HER-2. The reactivity of purified antibodies from immunized mouse sera was tested with (A) BT474 and (B) SKBR-3 breast cancer cell lines using flow cytometric analysis. Ab binding was detected with goat-anti mouse FITC-conjugated abs. The x-axis represents fluorescent intensity, and the y-axis represents relative cell number. Each histogram contains an overlay of mouse pre IgG, peptide antibodies, and AB2, a mouse mAb that binds HER-2. Both cell lines demonstrate that Abs from epitopes 563-598 and 585-598 do not recognize HER-2, while Abs from epitopes 597-626 and 613-626 recognize HER-2;

FIG. 30 shows wild-type FVB/n mice from FIG. 3B subcutaneously challenged with 3×106 NT2.5 cells and tumor growth monitored for 24 days. MVF-HER-2(266-296) cyclized- and noncyclized-treated mice had delayed tumor development (A) and growth (B) as compared to the MVF immunized mice only.

DETAILED DESCRIPTION OF EMBODIMENTS OF THE INVENTION

Figure 2:
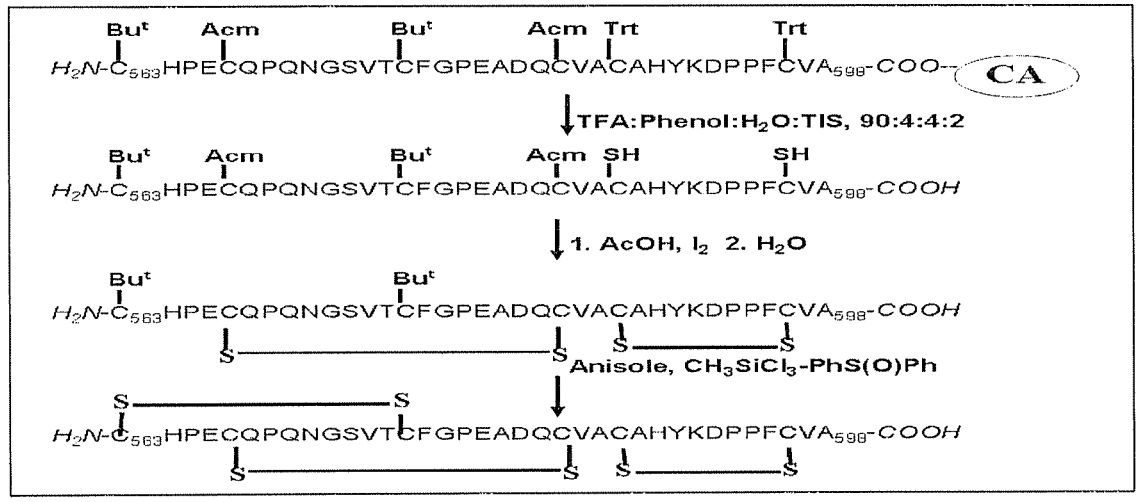
FIG. 2 shows the synthetic strategy for 3 disulfide pairings. Differential cysteine protection and selective removal and oxidation was used to generate the correct disulfide pairings as illustrated (SEQ ID NO: 27)

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

The present invention provides isolated polypeptides of the HER-2 protein, referred to hereinafter as HER-2 B epitopes. In some embodiments, the HER-2 B epitopes are immunogenic. The present invention additionally provides compositions that include one or more chimeric peptides, and the chimeric peptides include the HER-2 B epitopes. Additionally, compositions having one or more multivalent peptides are provided. These multivalent peptides include two or more of the HER-2 B epitopes. Methods of stimulating an immune response and methods of treating cancer in a subject are additionally provided. Vaccines are also provided for therapeutic and prophylactic use. The HER-2 B epitopes, either alone or in the context of chimeric peptides, as described herein, may capable of invoking a humoral response which results in the production of antibodies that are immunoreactive with the extracellular domain of the HER-2 protein. According to some embodiments, the HER-2 B epitopes or chimeric peptides confer a protective effect.

HER-2 protein, and its rat homolog neu, are transmembrane proteins with a relative molecular mass of 185 kd that is approximately 1255 amino acids (aa) in length. HER-2/neu protein has an extracellular binding domain (ECD) of approximately 645 aa, with 40% homology to epidermal growth factor receptor (EGFR), a highly hydrophobic transmembrane anchor domain (TMD), and a carboxyterminal cytoplasmic domain (CD) of approximately 580 aa with n 80% homology to EGFR. The amino acid sequence of the HER-2 protein and a nucleotide sequence which encodes such amino acid sequence are shown GenBank Accession No. M11730. FIG. 1 shows the amino acid sequence of the HER-2 protein (SEQ ID NO. 1).

The HER-2 B epitopes encompass peptides having one of the sequences, referred to hereinafter as the "reference sequences", and the sequences are:

```
CHPECQPQNGSVTCFGPEADQCVACAHYKDPPF    SEQ ID NO. 2
CVA, ;
```

```
VACAHYKDPPFCVA, ;                    SEQ ID NO. 3
```

```
                                             -continued
VARCPSGVKPDLSYMPIWKFPDEEGACQPL,;             SEQ ID NO. 4

IWKFPDEEGACQPL,;                             SEQ ID NO. 5

LHCPALVTYNTDTFESMPNPEGRYTFGASCV,;            SEQ ID NO. 6

ACPYNYLSTDVGSCTLVCPLHNQEVTAEDGTQR            SEQ ID NO 7
CEK,;

CPLHNQEVTAEDGTQRCEK,;                        SEQ ID NO. 8
or

CPINCTHSCVDLDDKGCPAEQRAS,.                   SEQ ID NO. 9
```

The HER-2 B epitopes may be cyclized or linear. When cyclized, the epitopes may be cyclized in any suitable manner. For example, disulfide bonds may be formed between selected cysteine (Cys) pairs in order to provide a desired confirmation. It is believed that the formation of cyclized epitopes may provide conformations that improve the humoral response, thus improving the protective effect.

The HER-2 B epitopes identified by SEQ ID NOS. 2-5 contain at least one region of the three regions that make contact with trastuzumab in the trastuzumab binding region of the HER-2 extracellular domain (SEQ ID NO. 1). In 2003, the crystal structure of the extracellular region of HER-2 alone and complexed to the Fab fragment of trastuzumab was published. Trastuzumab was shown to interact with three loops in subdomain IV comprising residues from SEQ ID NO. 1 in loop 1:579-583 (2 disulfide pairings between C563-C576, and between C567-C584), loop 2: 592-595 (cysteine disulfide pairing between C587-C596), and loop 3:615-625 (cysteine disulfide between C600-C623). Loops 1 and 3 are further stabilized by interaction with trastuzumab mainly through electrostatic interactions, whereas loop 2 take part in hydrophobic interactions.

The HER-2 B epitope identified by SEQ ID NO. 2 represents positions 563-598 of the HER-2 protein (SEQ ID. NO. 1). The HER-2 B epitope identified by SEQ ID NO. 2 may be cyclized by the formation of a disulfide bonds between Cys-563 and Cys-576, Cys-567 and Cys-584, and/or Cys-587 and Cys-596. The HER-2 B epitope identified by SEQ ID. NO. 3 represents positions 585-598. The HER-2 B epitope identified by SEQ ID NO. 3 may be cyclized by the formation of a disulfide bond between Cys-587 and Cys-596. The HER-2 B epitope identified by SEQ ID NO. 4 represents positions 597-626, and the underlined leucine (Leu) amino acid was mutated from Cys to Leu in order not to interfere with disulfide bond formation. The HER-2 B epitope identified by SEQ ID NO. 4 may be cyclized by the formation of a disulfide bond between Cys-600 and Cys-623. The HER-2 B epitope identified by SEQ ID NO. 5 represents positions 613-626, and the bold Leu amino acid was mutated from Cys to Leu in order not to interfere with disulfide bond formation as will be discussed further herein. It will be understood that the indicated Leu amino acids in SEQ ID NOS. 4 and 5 may alternatively be Cys.

The HER-2 B epitopes identified by SEQ ID NOS. 6-8 represent sequences designed to elicit antibody similar to the pertuzmab binding site of HER-2 (SEQ ID No. 1). The HER-2 B epitope identified by SEQ ID. NO. 6 represents positions 315-333 of the HER-2 protein (SEQ ID NO. 1). The HER-2 B epitope identified by SEQ ID NO. 6 may be cyclized by the formation of a disulfide bond between Cys-315 and Cys-331. The HER-2 B epitope identified by SEQ ID NO. 7 represents positions 298-333. The HER-2 B epitope identified by SEQ ID NO. 7 may be cyclized by the formation of disulfide bonds between Cys-299 and Cys-311 and/or Cys-315 and Cys-331. The HER-2 B epitope identified by SEQ ID NO. 8 represents positions 266-296. The HER-2 B epitope identified by SEQ ID NO. 8 may be cyclized by the formation of a disulfide bond between Cys-268 and Cys-295.

The HER-2 B epitope identified by SEQ ID NO. 9 represents positions 626-649. This sequence may have disulfide bonds between Cys-626 and Cys-634 and/or Cys-630 and Cys-634. It will be understood that each of epitopes having more than one Cys may be cyclized or linear.

As described herein, the HER-2 B epitopes also encompass peptides that are functional equivalents of the peptides identified by SEQ ID NOS. 2-9. Such functional equivalents have an altered sequence in which one or more of the amino acids in the corresponding HER-2 B epitope sequence is substituted or in which one or more amino acids are deleted from or added to the corresponding reference sequence. For example 1 to 3 amino acids may be added to the amino terminus, carboxy terminus, or both. In some examples, the HER-2 B epitopes are glycosylated.

In other examples, the HER-2 B epitopes may be the retro-inverso isomers of the HER-2 B epitopes. The retro-inverso modification comprises the reversal of all amide bonds within the peptide backbone. This reversal may be achieved by reversing the direction of the sequence and inverting the chirality of each amino acid residue by using D-amino acids instead of the L-amino acids. This retro-inverso isomer form may retain planarity and conformation restriction of at least some of the peptide bonds. For example, the nonretro-inverso form of SEQ ID. NO. 5 may be indicated as $NH_2$-L[IWKF-PDEEGACQPL]-COOH. The retro-inverso form of SEQ ID NO. 5 may be indicated as $NH_2$-D[LPQCAGEEDPFKWI]-COOH.

Nonconservative amino acid substitutions and/or conservative substitutions may be made. Substitutions are conservative amino acid substitutions when the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

In some examples, the deletions and additions are located at the amino terminus, the carboxy terminus, or both, of one of the sequences shown above. For example, the HER-2 B epitope equivalent has an amino acid sequence which is at least 70% identical, at least 80% identical, at least 90% identical, or at least 95% identical to the corresponding HER-2 B epitope sequences. Sequences which are at least 90% identical have no more than 1 alteration, i.e., any combination of deletions, additions or substitutions, per 10 amino acids of the reference sequence. Percent identity is determined by comparing the amino acid sequence of the variant with the reference sequence using MEGALIGN project in the DNA STAR program.

For functional equivalents that are longer than a corresponding HER-2 B epitope sequence, the functional equivalent may have a sequence which is at least 90% identical to the HER-2 B epitope sequence and the sequences which flank the HER-2 B epitope sequences in the wild-type HER-2 protein.

Functional equivalents of the HER-2 B epitopes may be identified by modifying the sequence of the epitope and then assaying the resulting polypeptide for the ability to stimulate an immune response, e.g., production of antibodies. For example, such assays may generally be performed by preparing a chimeric peptide which comprises the modified polypeptide and a Th epitope, injecting the chimeric peptide into a test animal and assaying for antibodies. Such antibodies may be found in a variety of body fluids including sera and ascites. Briefly, a body fluid sample is isolated from a warm-blooded animal, such as a human, for whom it is desired to determine whether antibodies specific for HER-2/neu polypeptide are present. The body fluid is incubated with HER-2/neu polypeptide under conditions and for a time sufficient to permit immunocomplexes to form between the polypeptide and antibodies specific for the protein and then assayed, preferably using an ELISA technique. In such technique, the calorimetric change is measured at 490 nm. Epitopes which induce production of antibodies that exhibit a titer equal to 10,000 or greater for HER-2/neu protein, may be useful. As used herein a titer of 10,000 refers to an absorbance value of 0.2 above background.

In accordance with other embodiments of the present invention, chimeric peptides and compositions comprising one or more chimeric peptides are provided. According to various embodiments, the chimeric peptides comprise a HER-2 B epitope, a T helper (Th) epitope, and a linker joining the HER-2 B epitope to the Th epitope. It will be understood that any suitable Th epitope may be used. For example, a promiscuous Th epitope may )e used. As used herein a "promiscuous" Th epitope is one which promotes release of cytokines that assists in bypassing MHC restriction. It will be further understood that any suitable linker may be used. For example, depending upon the Th epitope used, the HER-2 B epitope may be linked to either the amino or the carboxy terminus of the Th epitope. The location and selection of the Th epitope depends on the structural characteristics of the HER-2 B epitope, whether alpha helical or beta-turn or strand. Methods for selecting suitable Th epitopes are described in Kaumaya et al., "DE NOVO" ENGINEERING OF PEPTIDE IMMUNOGENIC AND ANTIGENIC DETERMINANTS AS POTENTIAL, VACCINES, in Peptides, Design, Synthesis and Biological Activity (1994), pp. 133-164, which is specifically incorporated herein by reference. A summary of the immune responses elicited a variety of Th epitopes containing B-cell epitope chimeras was presented in a review titled "Synthetic Peptides: Dream or Reality" by Kaumaya et al., and published in PEPTIDES IN IMMUNOLOGY, Wiley and Sons, Ltd. (1996).

In some examples, the Th epitope may be from about 14 to about 22, about 15 to 21, or 16 amino acids in length. In other embodiments, examples of suitable Th epitopes include, but are not limited to:

```
KLLSLIKGVIVHRLEGVE,;            SEQ ID NO. 10

NSVDDALINSTIYSYFPSV,;           SEQ ID NO. 11

PGINGKAIHLVNNQSSE,;             SEQ ID NO. 12

QYIKANSKFIGITEL,;               SEQ ID NO. 13

FNNFTVSFWLRVPKVSASHLE,;         SEQ ID NO. 14

LSEIKGVIVHRLEGV,;               SEQ ID NO. 15
```

-continued

```
FFLLTRILTIPQSLN,;               SEQ ID NO. 16
or

TCGVGVRVRSRVNAANKKPE,.          SEQ ID NO. 17
```

In other examples, the linker may be a peptide of from about 2 to about 15 amino acids, about 2 to about 10 amino acids, or from about 2 to about 6 amino acids in length. For example, the linker may be a peptide having the amino acid sequence Gly-Pro-Ser-Leu, SEQ ID NO. 18. The chimeric peptides may be linear or cyclized. Additionally, the HER-2 B epitopes, the Th epitopes, and/or the linker may be in retro-inverso form. Thus the HER-2 B epitope along could be in retro inverso form. Alternatively, the HER-2 B epitope and the Th epitope could be in retro inverso form. In another example, the HER-2 B epitope, the Th epitope, and the linker could be in retro inverso form.

Examples of suitable chimeric peptides include but are not limited to:

```
KLLSLIKGVIVHRLEGVE-GPSL-CHPECQPQNGSVT  SEQ ID NO. 19
CFGPEADQCVACAHYKDPPFCVA,;

KLLSLIKGVIVHRLEGVE-GPSL-VACAHYKDPPFCV  SEQ ID NO. 20
A,;

KLLSLIKGVIVHRLEGVE-GPSL-VARCPSGVKPDLS  SEQ ID NO. 21
YMPIWKFPDEEGACQPL,;

KLLSLIKGVIVHRLEGVE-GPSL-IWKFPDEEGACQ   SEQ ID NO. 22
PL,;

KLLSLIKGVIVHRLEGVE-GPSL-LHCPALVTYNTDT  SEQ ID NO. 23
FESMPNPEGRYTFGASCV,;

KLLSLIKGVIVHRLEGVE-GPSL-ACPYNYLSTDVGS  SEQ ID NO. 24
CTLVCPLHNQEVTAEDGTQRCEK,;

KLLSLIKGVIVHRLEGVE-GPSL-CPLHNQEVTAEDG  SEQ ID NO. 25
TQRCEK,;
or

KLLSLIKGVIVHRLEGVE-GPSL-CPINCTHSCVDLD  SEQ ID NO. 26
DKGCPAEQRAS,.
```

The peptides of SEQ ID NOS. 19-26 have a Th epitope, a GPSL linker (SEQ ID NO: 18) and a HER-2 B epitope.

The chimeric peptides and compositions comprising the peptides may be useful immunogens for inducing production of antibodies that interact with and bind to the extracellular domain of the HER-2 protein. The chimeric peptides may also be useful as laboratory tools for detecting antibodies to HER-2 protein in a subject's sera. The chimeric peptides may invoke an antibody response in a subject and that such antibodies may (a) immunopreciptate HER-2 protein, (b) bind to intact HER 2 receptor on ER-2 overexpressing cells in culture, and (c) reduce proliferation of HER-2 overexpressing cells in vitro. The chimeric peptides may also be used to immunize a subject and retard or prevent tumor development. The chimeric peptides may be used in vaccines to provide a protective effect.

In accordance with additional embodiments of the present invention, compositions comprising a mixture of two or more of the chimeric peptides are provided. In some examples, the HER-2 B epitope of each of the two or more chimeric peptides are different. In other examples, one of the HER-2 B epitopes is selected from SEQ ID NOS. 2-5 and another one of the HER-2 B epitopes is selected from SEQ IDS NOS. 6-8.

The HER-2 B epitopes and chimeric peptides may be synthesized using commercially available peptide synthesizers. For example, the chemical methods described in Kaumaya et al., "DE NOVO" ENGINEERING OF PEPTIDE IMMUNOGENIC AND ANTIGENIC DETERMINANTS AS POTENTIAL, VACCINES, in Peptides, Design, Synthesis and Biological Activity (1994), pp 133-164, which is specifically incorporated herein by reference, may be used.

For example, HER-2 B-cell epitopes may be synthesized co-linearly with the Th epitope to form a chimeric peptide. Peptide synthesis may be performed using Fmoc/t-But chemistry. The HER-2 B epitopes and chimeric peptides may be cyclized in any suitable manner. For example, disulfide bonds may be achieved using differentially protected cysteine residues, iodine oxidation, the addition of water to boost Acm removal and the concomitant formation of a disulfide bond, and/or the silyl chloride-sulfoxide method.

The HER-2 B epitopes and chimeric peptides may also be produced using cell-free translation systems and RNA molecules derived from DNA constructs that encode the epitope or peptide. Alternatively, the epitopes or chimeric peptides are made by transfecting host cells with expression vectors that comprise a DNA sequence that encodes the respective epitope or chimeric peptide and then inducing expression of the polypeptide in the host cells. For recombinant production, recombinant constructs comprising one or more of the sequences which encode the epitope, chimeric peptide, or a variant thereof are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

The HER-2 B epitope and chimeric peptide may be expressed in suitable host cells, such as for example, mammalian cells, yeast, bacteria, insect cells or other cells under the control of appropriate promoters using conventional techniques. Suitable hosts include, but are not limited to, E. coli, P. pastoris, Cos cells and 293 HEK cells. Following transformation of the suitable host strain and growth of the host strain to an appropriate cell density, the cells are harvested by centrifugation, disrupted by physical or chemical means, and the resulting crude extract retained for further purification of the epitope or chimeric peptide.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate the recombinant polypeptide.

To produce glycosylated epitopes and chimeric peptides, recombinant techniques may be used. For example, mammalian cells such as, Cos-7 and Hep-G2 cells be employed in the recombinant techniques. Alternatively, glycosylated epitopes and chimeric peptides may be produced using standard Fmoc/tBut synthesis. For example, one or more sugar units can be added to peptides using a chemoenzymatic approach employing endo-β-N-aceylglucosaminidases as the key enzyme for oligosaccharide transfer.

Naturally occurring variants of the HER-2 B epitopes may also be isolated by, for example, by screening an appropriate cDNA or genomic library with a DNA sequence encoding the polypeptide.

In accordance with further embodiments, multivalent peptides which comprise a plurality, i.e., at least two of the HER 2-B epitopes or functional equivalents thereof and a Th epitope are provided. The HER-2 B epitopes and Th epitope are connected to a template. For example, the HER-2 B epitopes and the Th epitope may be connected to a core β sheet template. In another example, the template may be two strands of alternating leucine and lysine residues, which are connected by a linker. The linker is an amino acid or a peptide of from about 2 to about 15 amino acids, from about 2 to about 10 amino acids, or from about 2 to about 6 amino acids in length. For example, the linker may be the amino acid sequence Gly-Pro-Ser-Leu, SEQ ID NO. 18.

Multivalent peptides may be synthesized in any suitable manner. For example, multivalent peptides may be prepared by employing a combinatorial Fmoc/tbutyl, Fmoc/benzyl and Boc benzyl strategy as well as a fourth level of differential protecting group (Npys) strategy. Details of such approach are presented in Larimore et al. (1995) Journal of Virology 69:6077-6089, which is specifically incorporated herein by reference.

In accordance with yet other embodiments of the present invention, isolated polynucleotides which encode the HER-2 B epitopes and the chimeric peptides discussed herein are provided. The present polynucleotides also encompass polynucleotides having sequences that are capable of hybridizing to the nucleotide sequences of the HER-2 B epitopes or the chimeric peptides under stringent conditions, and/or highly stringent conditions. Hybridization conditions are based on the melting temperature (Tm) of the nucleic acid binding complex or probe, as described in Berger and Kimmel (1987) Guide to Molecular Cloning Techniques, Methods in Enzymology, vol 152, Academic Press. The term "stringent conditions", as used herein, is the "stringency" which occurs within a range from about Tm-5 (5° below the melting temperature of the probe) to about 20° C. below Tm. As used herein "highly stringent" conditions employ at least 0.2×SSC buffer and at least 65° C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Polynucleotides comprising sequences encoding a HER-2 B epitope or a chimeric peptide of the present invention may be synthesized in whole or in part using chemical methods or recombinant methods which are suitable. Polynucleotides which encode a HER-2 B epitope may be obtained by screening a genomic library or cDNA library with antibodies immunospecific for the HER-2 protein to identify clones containing such polynucleotide.

The polynucleotides are useful for producing a HER-2 B epitope or a chimeric peptide. For example, an RNA molecule encoding a multivalent chimeric peptide may be used in a cell-free translation systems to prepare such polypeptides. Alternatively, a DNA molecule encoding a HER-2 B epitope or a chimeric peptide may be introduced into an expression vector and used to transform cells. Suitable expression vectors include, but are not limited to, chromosomal, nonchromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovirus, fowl pox virus, pseudorabies, baculovirus, and retrovirus. The DNA sequence may introduced into the expression vector by any suitable procedure.

In accordance with further embodiments, recombinant constructs comprising one or more of the polynucleotides encoding one or more HER-2 B epitopes or chimeric peptides are provided. Suitable constructs include, for example, vectors, such as a plasmid, phagemid, or viral vector, into which a sequence that encodes the HER-2 B cell epitope or the chimeric peptide has been inserted. In the expression vector, the DNA sequence which encodes the epitope or chimeric peptide is operatively linked to an expression control sequence, i.e., a promoter, which directs mRNA synthesis. Representative examples of such promoters, include the LTR or SV40 promoter, the *E. coli* lac or trp, the phage lambda PL promoter and other promoters known to control expression of genes in prokaryotic or eukaryotic cells or in viruses. The expression vector may also contain a ribosome binding site for translation initiation and a transcription terminator. For example, the recombinant expression vectors also may include an origin of replication and a selectable marker, such as for example, the ampicillin resistance gene of *E. coli* to permit selection of transformed cells, i.e., cells that are expressing the heterologous DNA sequences. The polynucleotide sequence encoding the HER-B cell epitope or the chimeric peptide may be incorporated into the vector in frame with translation initiation and termination sequences. For example, the polynucleotide may further encode a signal sequence which is operatively linked to the amino terminus of the HER-2 B epitope or chimeric peptide.

The polynucleotides encoding the HER-2 B epitope or the chimeric peptides comprising such epitopes may be used to express recombinant peptide using suitable techniques. Such techniques include, but are not limited to, those described in Sambrook, J. et al (1989) Molecular Cloning A Laboratory Manual, Cold Spring Harbor Press, Plainview, N.Y. and Ausubel, F. M. et al. (1989) Current Protocols in Molecular Biology, John Wile & Sons, New York, N.Y. Polynucleotides encoding the HER-2 B epitope or the chimeric peptides comprising such epitopes may also be used to immunize subjects.

In accordance with yet further embodiments, methods of treating cancer are provided. The methods comprise administering a pharmaceutical composition to a subject. In other embodiments, vaccines comprising at least one chimeric peptide, multivalent peptide, or both, of the polynucleotide which encodes the same are provided. The pharmaceutical composition comprises a pharmaceutically acceptable vehicle and at least one chimeric peptide, multivalent peptide, or both, or the polynucleotide which encodes the same, as described herein. Pharmaceutically acceptable vehicles, include, but are not limited to pharmaceutically acceptable carriers, excipients or diluents. These vehicles are generally nontoxic to subjects at the dosages and concentrations employed.

In addition to the epitopes, multivalent peptides, and chimeric peptides or the polynucleotide which encodes the same, other components, such as a vehicle for antigen delivery and immunostimulatory substances designed to enhance the protein's immunogenicity are included in the pharmaceutical composition. Examples of vehicles for antigen delivery include aluminum salts, water-in-oil emulsions, biodegradable oil vehicles, oil-in-water emulsions, biodegradable microcapsules, and liposomes. For the vaccines which comprise the chimeric peptide, a suitable vehicle for antigen delivery is a biodegradable microsphere, which may be comprised of poly (D, L-lactide-co-glycolide) (PLGA).

While any suitable vehicle may be employed in the pharmaceutical compositions of this invention, the type of carrier will vary depending on the mode of administration and whether a substantial release is desired. For parenteral administration, such as subcutaneous injection, the carrier may be water, saline, alcohol, a fat, a wax, or a buffer. Biodegradable microspheres (e.g., polylactic galactide) may also be employed as vehicles for the pharmaceutical compositions of this invention. According to some embodiments, the pharmaceutical composition comprises an adjuvant.

The HER-2 chimeric and multivalent peptides and the polynucleotides which encode the same may be useful for enhancing or eliciting, in a subject or a cell line, a humoral response and, preferably, a cellular immune response (e.g., the generation of antigen-specific cytolytic T cells). In some examples the subject is a human. A subject may be afflicted with cancer or other cancer involving HER-2, such as breast cancer, or may be normal (i.e., free of detectable disease and infection). The pharmaceutical compositions and vaccines may be useful for treating women who have a family history of breast cancer or who have had breast tumors removed. According to some embodiments, "treating" means inhibiting or slowing or retarding the growth of the tumor. Such cancers include, but are not limited to, breast, lung, ovarian, bladder and prostate. In some examples, multiple intramuscular injections, at three week intervals, are used to administer the pharmaceutical composition.

EXAMPLES

Exemplary methods are described below, although methods and materials similar or equivalent to those described herein can be used in the practice or testing of the present peptides, compositions and methods. All publications and other references mentioned herein are incorporated by reference in their entirety. The materials, methods, and examples are illustrative only and not intended to be limiting.

Peptide Synthesis and HPLC Purification. Peptides were synthesized as previously described (Kaumaya 1994). Briefly, peptides were synthesized on a Milligen/Biosearch 9600 peptide synthesizer, using a 4-methylbenzhydrylamine resin as the solid support (substitution 0.54 mm/g). The Fmoc/t-butyl synthetic method was employed using 4-(hydroxymethyl) phenoxyacetic acid as the linker. After the final deprotection step, protecting groups and peptide resin bond were cleaved with 90% TFA, 5% anisole, 3% thioanisole, 2% ethanedithiol. Crude peptide was purified by semipreparative HPLC using a Vydac C4 (10 mm×25 cm) column at 32.5° C. Buffers were 0.1% TFA in $H_2O$ and 0.1% TFA in acetonitrile. Peptides incorporate a "promiscuous" T cell epitopes MVF 288-302 (Kaumaya 1994): DW1MVF (HER-2 376-395), MVFDW4 (628-647), DW5MVF (115-136), DW6MVF (410-429).

Gel Filtration. 20 mg/ml acidified peptide solution (0.1 mg/ml in DTT) was loaded onto a Sephadex G-25 column and 5 ml fractions eluted with 0.1M HOAc. Peptide samples were measured spectrophotometrically at 235 nm and absorbance values plotted vs. time. Samples with absorbance values above 0.1 and eluting before DTT were pooled and lyophilized. The reaction was monitored for completion by Ellman's reagent at 410 nm.

Capillary Zone Electrophoresis. CZE was performed on a Beckman P/ACE System 2100 interfaced with an IBM computer. Sample was voltage separated (15 kV) in 100 mM sodium borate using a 50 cm capillary over 20 min. Eluant was monitored at 214 nm.

Circular Dichroism and mass spectrometry. Measurements were performed on a JASCO J-500 spectropolarimeter interfaced with an IBM computer. The instrument was calibrated in 0.06% (w/v) solution of ammonium-d-10-camphorsulfonate. The CD spectra of the peptides (62.5-250 uM by dilution of peptide stocks in water) were measured at ambient temperature in a 0.1 cm path length cylindrical quartz cuvette (Hellma). Mean residue ellipticity (mdeg) was calculated using the relationship $[\theta]=100\,\theta/cnl$ where is the ellipticity, c is the peptide concentration (mM), n is the number of amino acids in the peptide, and 1 is the path length (cm). Fast atom bombardment (FAB) mass spectrometry measurements were carried out on a inneganMat-900 instrument.

Mercuric Acetate. Peptide was dissolved in a minimal amount of water and 100 mg/mm S-tBu solution (2-10 fold excess) added. Peptide was placed under vacuum and precipitated by 2-Mercaptoethanol in a 55° C. water bath under stirring. After filtering through dampened Celite, the filtrate was rotary evaporated, acidified with 0.1% TFA in water and lyophilized.

Biological Procedures

Immunizations and animals. Female New Zealand white rabbits were obtained from Mohican Valley Rabbitry (Loudenville, Ohio). Rabbits were immunized subcutaneously at multiple sites with a total of 1 mg of peptide emulsified in CFA. Subsequent booster injections (1 mg and 500 µg in PBS) were given three and six weeks after the primary immunization. Sera were collected and complement inactivated by heating to 56° C. for 30 min. Sera aliquots were stored at −5 to −15° C. Antibodies were purified by ammonium sulfate precipitation: A stock solution of saturated ammonium sulfate solution (SAS) was prepared, autoclaved and cooled to 4° C. Antibody was allowed to precipitate by slowly adding SAS to 35% v/v under stirring in cold room. Samples were centrifuged 14,000×g 20 min and the supernate stored at −20° C. The pellet was dissolved with 0.1M PBS in ½ original volume. Fractions were then placed in Slide-a-lyzer cassettes (Pierce) and dialyzed against frequent changes of >200 volumes pH 8, 0.15M NaCl. The saline was brought to pH 8 with a few drops of 0.1M NaOH. IgG concentration was determined by radial immunodiffusion (RID) (The Binding Site, UK). Monoclonal antibodies were purchased from Oncogene Science.

Direct ELISA. U-bottom polyvinyl chloride plastic assay plates were coated with 100 µl of antigen at 2 µg/ml in PBS overnight at 4° C. Nonspecific binding sites were blocked for 1 hour with 200 µl PBS-1% BSA and plates were washed with PBT (phosphate-buffered saline containing 0.05% Tween 20 and 1% horse serum). Rabbit antiserum 1/500 or mouse antiserum 1/50 in PBT was added to antigen coated plates, serially diluted 1:2 in PBT, and incubated 2 hr at room temperature. After washing the plates, 50 µl of 1/500 goat anti-rabbit or goat anti-mouse IgG conjugated to horseradish peroxidase (Pierce Chemical Co.) was added to each well. Excess antibody conjugate was removed, and bound antibody was detected using 50 µl of 0.15% $H_2O_2$ in 24 mM citric acid, 5 mM sodium phosphate buffer, pH 5.2, with 0.5 mg/ml 2,2'-aminobis(3-ethylbenzthiazoline-6-sulfonic acid) as the chromophore. Color development was allowed to proceed for 10 min and the reaction was stopped with 25 µl of 1% sodium dodecylsulfate. Absorbance was determined at 410 nm using a Dynatech MR700 ELISA reader. Results are expressed as the mean absorbance of duplicate wells after subtraction of background.

Cell Culture. Stock cultures were maintained at 37° C. in a 5% $CO_2$ incubator. All cell culture media, FCS, and supplements were purchased from GEBCO (Grand Island, N.Y.). The human breast adenocarcinoma cell lines SKBR-3 and MCF-7 were obtained from the American Type Culture Collection and was subcultured in McCoy's 5A or DMEM supplemented with 10% FCS and L-glutainine. Cav-1 was maintained in RPMI 1640 with 10% FCS and L-glutamine. Cav-was derived from a fresh colon tumor specimen which was cryopreserved and subsequently cultured; it does not express detectable levels of HER-2/neu. SKBR3 is a breast tumor cell line which overexpresses the HER-2 protein while MCF-7 expresses the normal concentration of protein.

Immunoprecipitation and Western Blotting. On day zero, $1.0\times10^7$ SKBR3 cells were plated in 75 $cm^3$ cell culture flasks and allowed to adhere overnight. Anti-peptide antibodies were added (100 µg/ml) for 4 hrs. The reaction was stopped by aspirating the media and immediately adding ice cold 0.1M phosphate buffered saline (PBS). Cells were trypsinized and washed twice with cold Hank's Balanced Salts Solution (HBSS). Cold lysis buffer (150 mM NaCl; 50 mM Tris, pH 8; 10 mM EDTA, 10 mM sodium pyrophosplhate, 10 mM sodium fluoride; 1% NP-40, 0.1% SDS) containing 3 mM $Na_3VO_4$, 10 µg/ml each aprotinin and leupeptin was added to cells resuspended in 100 µl HBSS. Lysis was achieved by gentle rotation at 4° C. for 20 min. After centrifugation (14,000×g, 20 min) to remove cell debris, lysates were incubated with 3-5 µg antibody and 30 µl Protein A/Protein G (Oncogene Science) overnight. Beads were pelleted by centrifugation (14,000×g 30 sec),washed twice in lysis buffer containing 1 mM $Na_3VO_4$ and boiled in SDS sample buffer 5 min.

Proteins were resolved by 7.5% SDS-PAGE, transferred to nitrocellulose and probed with antibody. Protein transfer was monitored with prestained molecular mass standards (Bio-Rad). Immunoreactive bands were detected using horse radish peroxidase conjugated goat anti rabbit immunoglobulin by enhanced chemiluminescence (Amersham)

Indirect Binding Assay. SKBR3 cells or MCF-7 cells were plated at 5,000 cells/well in V-bottom plates (Linbro, McLean Va.). The cells were incubated with various concentrations of antibodies. After being washed with Hank's Balanced Salts Solution (HBSS) the cells were incubated for one hour with fluorescein isothiocyanate (FITC)-conjugated goat anti-rabbit or goat anti-mouse antibody and fixed with formalin. A mouse monoclonal Ab (Oncogene Science, Cambridge, Mass.) was used as the positive control and an anti-CD3 Ab as the negative control. The cells were analyzed by a Coulter ELITE flow cytometer (Coulter, Hialeah, Fla.), which has an argon laser for excitation at 488 mn, and a 525run band pass filter for FITC fluorescence $5.0\times10^3$ cells were counted for each sample and final processing was performed. Debris, cell clusters and dead cells were gated out by light scatted assessment before single parameter histograms were drawn.

Effect of Abs on cell proliferation. SKBR3, MCF7 and CAVI cells were plated 5,000 cells/well in V-bottom plates along with various concentrations of Ab on day zero. On day 3, cells were pulsed with [3H] thymidine (1 µCi/well) at which time they were placed in a 20° C freezer for 1 h. After thawing at room temperature cells were harvested an a PHD cell harvester (Cambridge Tech, Inc.). Samples were incubated in 5 ml Ready Safe liquid scintillation cocktail (Beckman) and radioactivity determined by beta counter. Results are expressed as the mean CPM +/−the standard deviation (SD).

CTL Assay: In vitro stimulation. Inguinal and periaortic lymph nodes (LN) are removed 7-10 days after immunization. LN cells ($4\times10^6$–$5\times10^6$) are then stimulated in vitro by coculturing with $1.5\times10^5$ irradiated (10 000 rad) P815 cells prepulsed for 1 h with 1 µM of the appropriate CTL peptide. The culture medium used is cDMEM (DMEM supplemented with 10% FCS). Supernatant containing 30 U/ml (final) of IL-2, 2 mM L-glutamine, 10 mM Hepes and $5\times10^5$ M-2-mercaptoethanol).

Seven days after in vitro stimulation, the CTL activity is tested in a standard chromium-release assay. P815 cells ($10^6$) are labeled with 150 μCi sodium [$^{51}$Cr] clromate for 1 h at 37° C. in the presence or absence of the appropriate peptide (1 μM) and washed three times. Labeled targets ($2\times10^3$) are co-incubated with stimulated LN cells at predetermined ratios in 200 μl volumes in V-bottom 96 well plates. After a 4 h incubation at 37° C., the supernatants (100 μl) are harvested for γ-counting. The % specific lysis is calculated as 100× [(experimental-spontaneous release)/(total-spontaneous release)] (Valmori, et al. 1994).

Effect of antibodies in vivo. HER2 cells ($3\times10^6$) were suspended in 250 ul PBS, mixed with 250 μl MATRIGEL (Beckton Dickinson) on ice and injected subcutaneously into mice. Polyclonal antibodies to a total concentration of 2 mg/mouse, were injected i.p. on days 9 and 11. Tumor volume was measured twice weekly with calipers and calculated by the formula (length×width×height).

Example 1

A Conformational HER-2 B-Cell Epitope Incorporating of Two Native Disulfide Bonds Show Enhanced Tumor Cell Binding.

The human EGFR disulfide pairings have been defined. Based on the high homology between EGFR and HER-2, the 628-647 epitope to 626-649 to incorporate two disulfide bonds between Cys-626 and Cys-634, and Cys-630 and Cys-642. Differential side chain protection and a specialized deprotection and oxidation successfully generated the cyclized product with a desired secondary structural characteristics as determined by CD measurements. Both linear and cyclized constructs were highly immunogenic (titers >200,000) in outbred mice. Flow cytometry analysis showed that the antibodies against the cyclized epitope bound the HER-2 protein with a higher affinity than the non-cyclized epitope (mean log fluorescence 2.29 and 1.65 respectively). Antibodies against both the cyclized and non-cyclized epitopes were able to cause a reduction of growth in cells overexpressing HER-2 as measured in an anchorage-independent growth assay (31 and 58% inhibition, respectively). Antibodies against both constructs were able to elicit IFN-γ release in the presence of effector human PBMCs, with the cyclized antibodies inducing 25% higher levels of IFN-γ compared to the linear antibodies. Cyclized antibodies elicited twice the level of specific lysis compared to non-cyclized antibodies in an ADCC assay (11 and 5.6% respectively). To investigate the in vivo effect of these peptide vaccines, inbred FVB/N mice were immunized with the constructs. Both constructs were immunogenic in these mice with the cyclized construct generating higher titers. These mice were then challenged with the NT2.5 tumor cell line which has an FVB/N background. The mice immunized with the cyclized conformational construct had a reduction in tumor volume compared to both the linear and control MVF immunized mice. Cyclized vaccinated mice had the longest doubling time (6.63 days), thereby demonstrating the greatest ability to impede tumor growth compared to linear or MVF control peptide (4.31 and 4.48 days, respectively). Thus, these results show that conformational peptides for eliciting high affinity Abs has immediate application for the design of effective Her-2 vaccines.

Example 2

Design and Synthesis of Novel HER-2 B-Cell Epitopes

Four new constructs were selected for synthesis as shown in Table 1. All four constructs contain as least one region of the three regions that make contact with trastuzumab. HER-2 B epitopes were synthesized co-linearly with the MVF promiscuous Th epitope. Peptide synthesis was performed using Fmoc/t-But chemistry. The formation of three disulfide bonds for epitope 563-598 was achieved using differentially protected cysteine residues shown in FIG. 2. The first disulfide bond is formed using iodine oxidation. The addition of water boosts Acm removal and the concomitant formation of a disulfide bond between C567 and C584. The final disulfide bond between C563 and C576 was formed using the silyl chloride-sulfoxide method.

TABLE 1 shows candidate peptide vaccines from the HER-2/Herceptin structure (SEQ ID NOS 19-22 are disclosed respectively in order of appearance. The promiscuous T-helper epitope sequence, shown in italics, is linked to the B-cell epitope via a four residue turn sequence (GPSL); SEQ ID NO:18). Underlined amino acids were mutated from Cys to Leu so as not to interfere with natural disulfide formation.

| Designation | Peptide | Sequence | M. Wt. (da) |
|---|---|---|---|
| MVF 563 SS | 563-598 peptide with 3 disulfide bonds | H$_2$N-*KLLSLIKGVIVHRLEGVE*-GPSL-CHPECQPQNGSVTCFGPEADQCVACAHYKDPPFCVA-COOH | 6181 |
| MVF 585 SS | 585-598 peptide with one disulfide bond | H$_2$N-*KLLSLIKGVIVHRLEGVE*-GPSL-VACAHYKDPPFCVA-COOH | 3856 |
| MVF 597 SS | 597-626 peptide with one disulfide bond | H$_2$N-*KLLSLIKGVIVHRLEGVE*-GPSL-VARCPSGVKPDLSYMPIWKFPDEEGACQPL-COOH | 5672 |
| MVF 613 | 613-626 peptide | H$_2$N-*KLLSLIKGVIVHRLEGVE*-GPSL-IWKFPDEEGACQPL-COOH | 3977 |

Example 3

Immunogenicity of HER-2 Peptides

Figure 3:
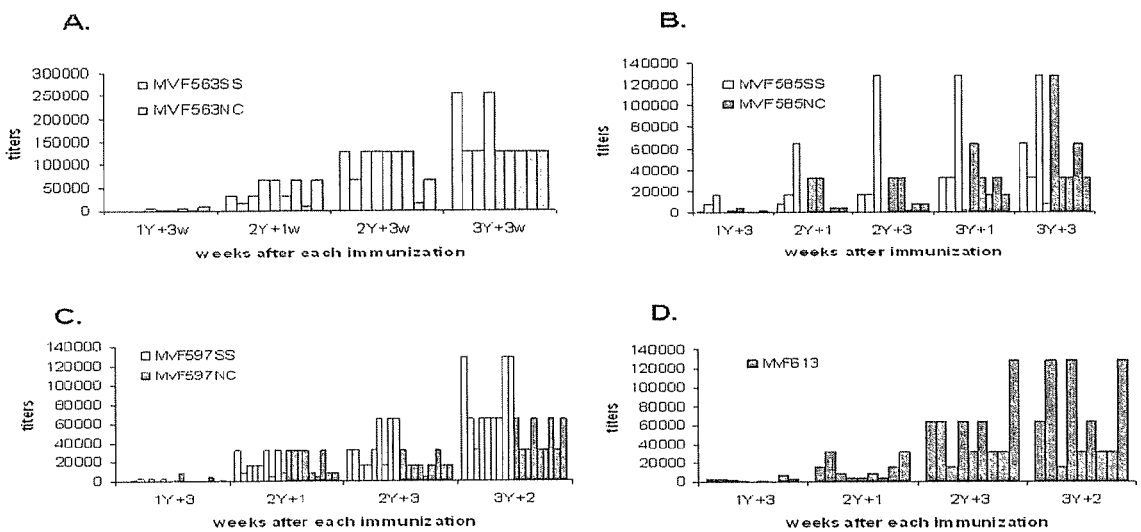
FIG. 3 shows the immune response in FVB/n mice. Groups of four to ten FVB/n mice were immunized with linear (NC) or disulfide-bonded (SS) peptide constructs (A) MVF563-598, (B) MVF585-598, (C) MVF597-626, or the linear peptide (D) MVF613-626. Each mouse is represented as an individual bar. Note that the scale in A is different then B-D.

The immunogenicity of the 4 constructs listed in Table 1 was determined using both the disulfide-bonded and linear constructs by immunizing groups of FVB/n mice (n=4-9)6-8 weeks old. Both 563-598 cyclized and non-cyclized constructs was highly immunogenic (FIG. 3A); by three weeks after the third immunization all mice had titers above 120,000 and two mice with the cyclized construct (MVF563SS) had titers above 250,000. The 585-598 construct proved to be the least immunogenic (FIG. 3B), three weeks after the third immunization only one mouse from both the cyclized (SS) and linear (NC) groups had a titer above 120,000 with a mean titer around 58,000. Both the 597-626 and 613-626 peptide constructs were highly immunogenic (FIG. 3 C, D). Three mice that received the cyclized form of 597-626 had titers above 120,000, while no mouse that received the linear form had titers above 120,000.

Second, we tested the immunogenicity of the B-cell epitopes in neu-N transgenic mice developed by Guy et al. The neu-N transgenic mice elicited high titers of Abs (data not shown) to the peptide constructs similar to those seen in FVB/n mice even though these mice have low basal levels of neu specific IgG upon vaccination with a neu-specific whole-cell vaccine.

Example 4

Cross Reactivity of Herceptin Binding Peptides with Herceptin (Trastuzumab)

Figure 4:
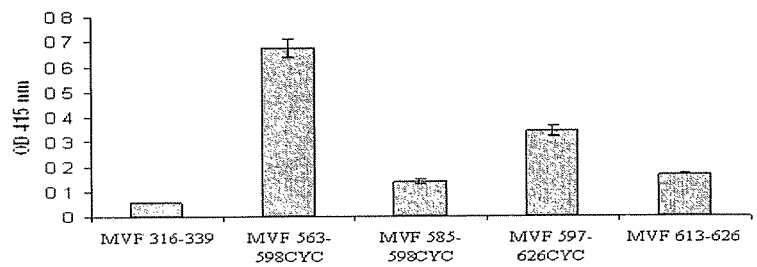
FIG. 4 shows that trastuzumab specifically recognizes peptide epitopes designed to mimic the trastuzumab binding-site of HER-2. The peptide sequences are given on the x-axis. MVF316-339 is an Her-2 irrelevant control peptide.

Whether the conformational peptides from trastuzumab binding sites could recognize herceptin by ELISA was tested. As shown in FIG. 4, various peptides in the binding region of 563-626 bound trastuzumab. Maximum binding occurred with cyclized epitope 563-598 which possesses the 3 disulfide pairings. This result is in contrast with the FACS binding of antibodies to HER-2 due to glycosylation.

Example 5

Cross-Reactivity of Peptide Antibodies with HER-2 Protein

Figure 5:
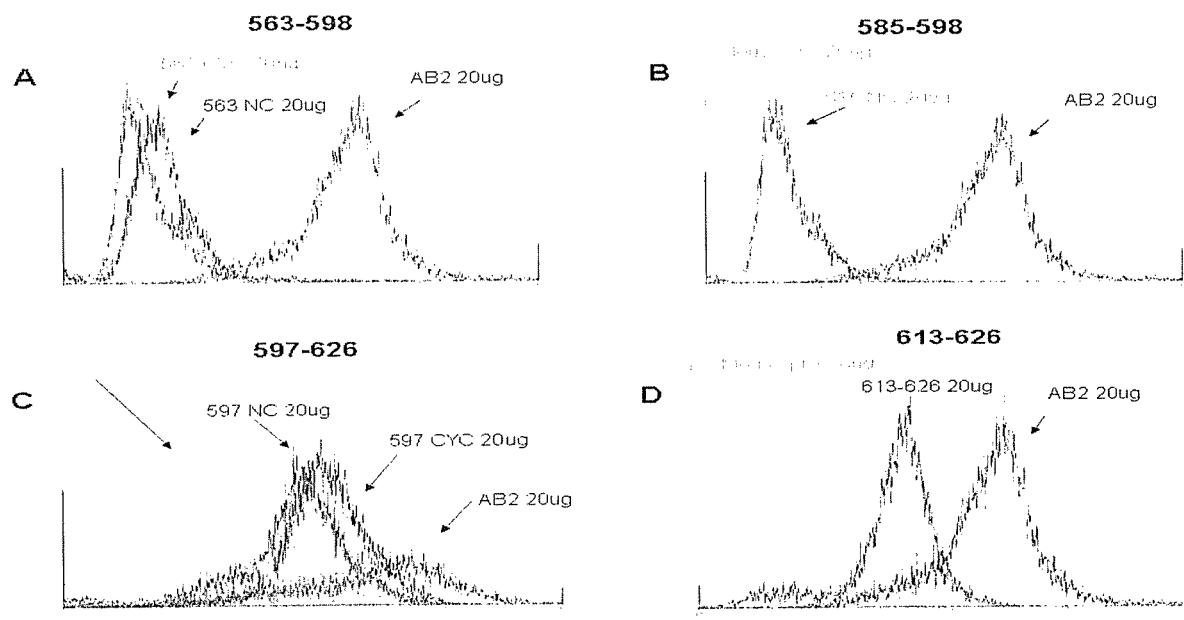
FIG. 5 shows the flow cytometry of peptide-specific antibodies with human breast cancer cells over-expressing HER-2. Flow cytometry was used to assess whether antibodies from FVB/n mice induced by various constructs recognize native HER-2. BT-474 human breast cancer cells (HER-2high) were treated with 10 μg/mL of normal mouse Ig (negative control), mouse monoclonal Ab-2 (positive control), or peptide antibodies raised in FVB/n mice.
Figure 6:
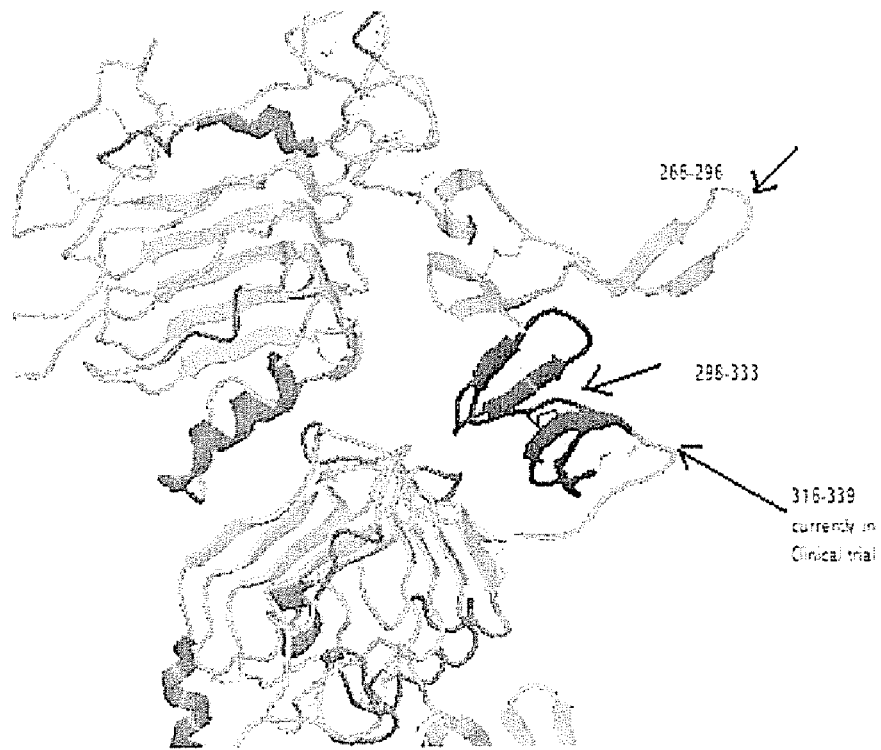
FIG. 6 shows the pertuzumab binding sites with HER-2.
Figure 7:
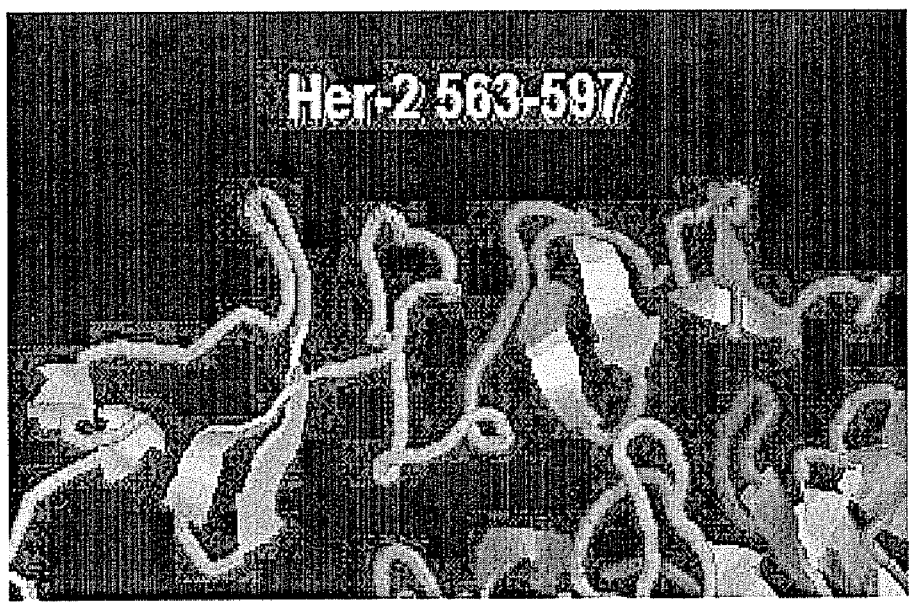
FIG. 7 shows the 3-dimensional structure of Herceptin Peptide epitopes.
Figure 8:
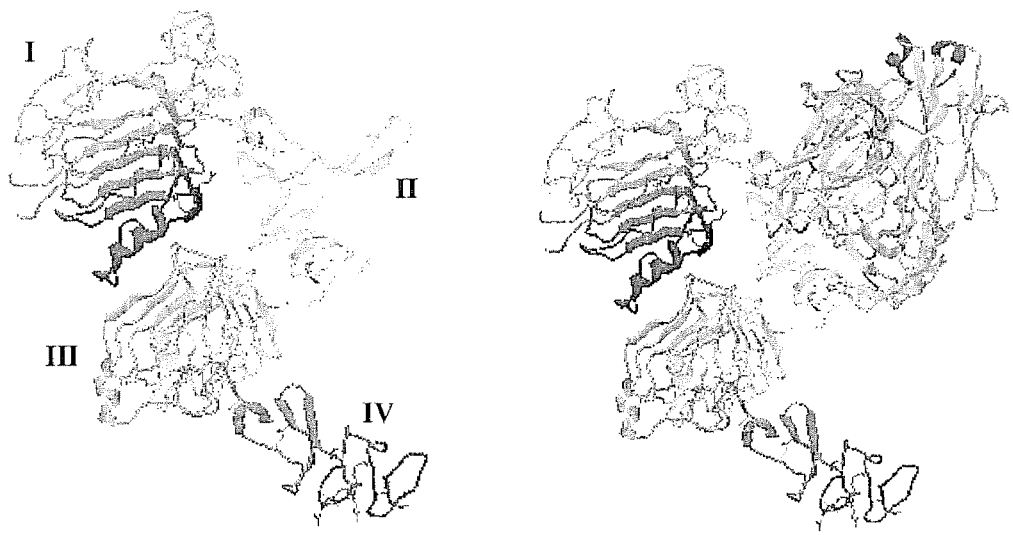
FIG. 8 shows the structure of HER-2 bound to Omnitarg™ (Pertuzumab)
Figure 9:
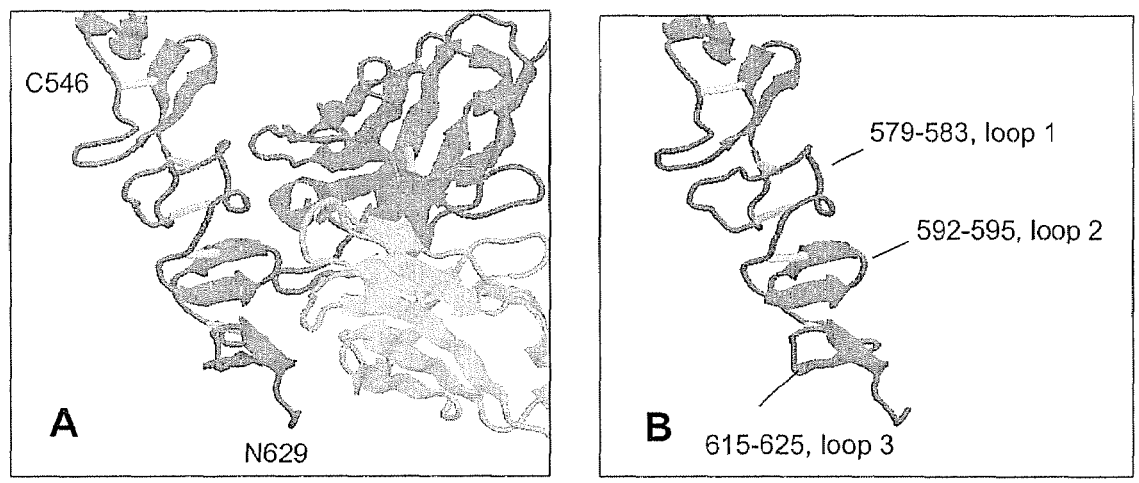
FIG. 9 shows the HER-2-trastuzumab binding site. (A) Ribbon diagram of HER-2 and the heavy and light chain of trastuzumab complex. (B) The trastuzumab binding-site of HER-2. This region is disulfide-rich. The sequences of the three loops that interact with trastuzumab are indicated.
Figure 10:
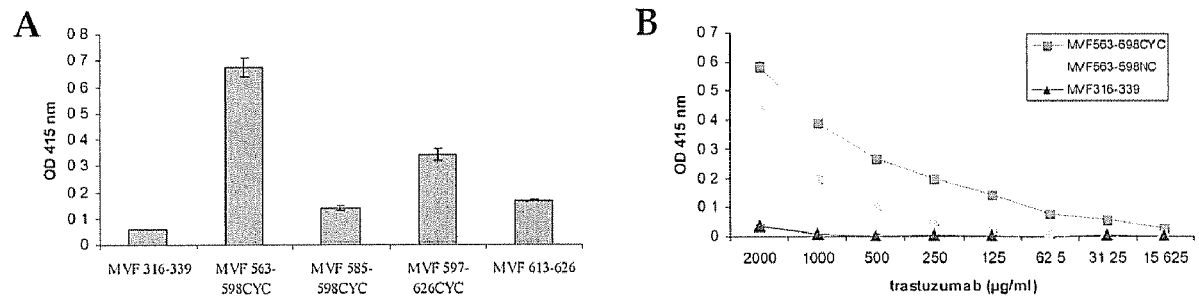
FIG. 10 shows the binding of trastuzumab to peptides. Microtiter wells were coated overnight with 2 μg/ml of various peptides and then blocked with 1% BSA for one hour. Trastuzumab was then added to plates at a concentration of 2000 μg/ml and serially diluted 1:2 with PBT. Bound trastuzumab was detected with HRP-conjugated anti-human IgG and then with substrate. (A) The $OD_{415}$ value for peptides from Table I and an irrelevant control peptide (MVF316-339) using 2000 μg/ml of trastuzumab. Values shown are the mean of duplicate samples. SEM are indicated by error bars. (B) Titration of trastuzumab with the disulfide-bound (CYC) and linear (NC) forms of MVF563-598 along with irrelevant control peptide (MVF316-339).
Figure 11:
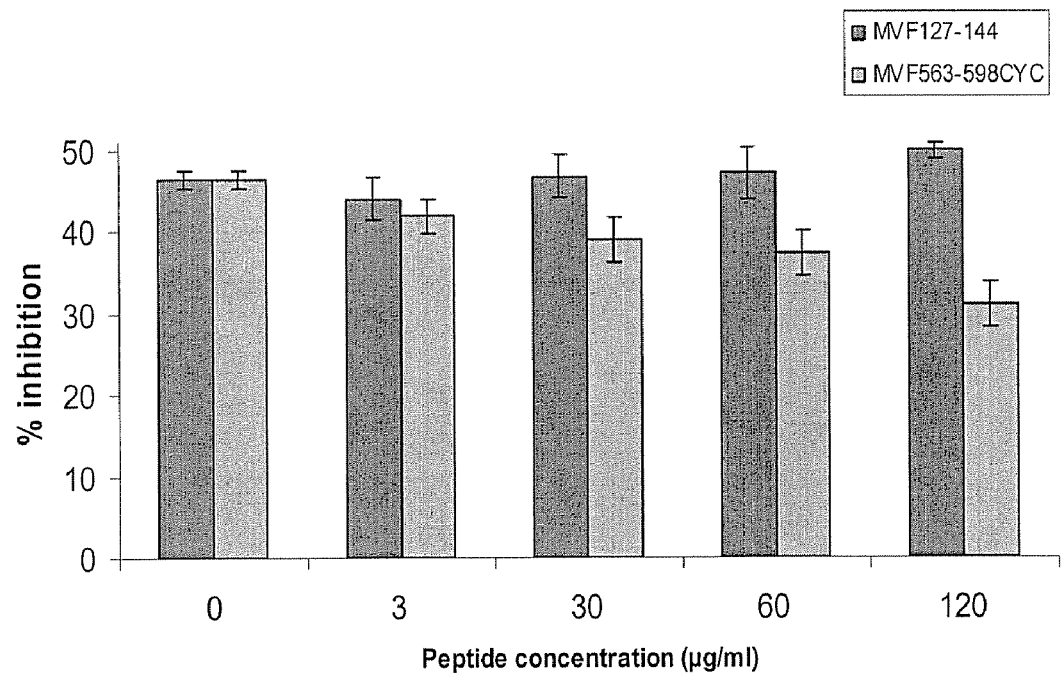
FIG. 11 shows cell proliferation by MTT assay. BT474 cells were plated in 96-well microtiter plates at 2×104 cells/well and incubated overnight at 37° C. PBS containing trastuzumab or normal human IgG (100 μg/ml) with or without peptide at the indicated concentrations was added to the wells. The plates were incubated for three days at 37° C. The number of viable cells was measured with MTT by reading $OD_{570}$. The percentage of inhibition was calculated using the formula $(OD_{normal\ human\ IgG} - OD_{trastuzumab} + \text{peptide}) / OD_{normal\ human\ IgG} \times 100$. Values shown are the mean of triplicate samples. SEM are indicated by error bars.
Figure 12:
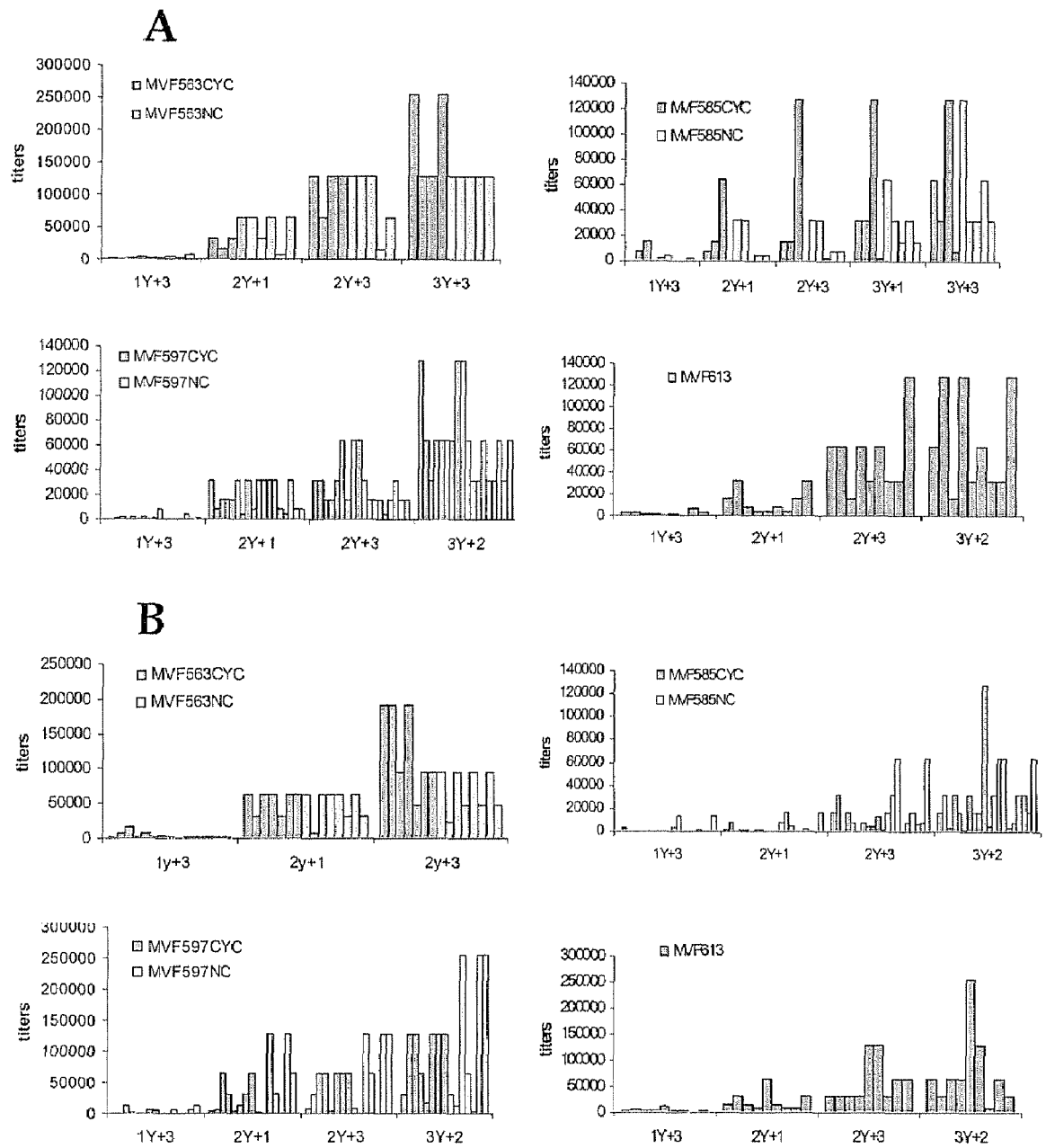
FIG. 12 shows the antibody response against peptides in FVB/n (A) and Neu-N (B) transgenic mice. Direct ELISAs were performed on sera from mice immunized with the cyclized (CYC) and linear (NC) constructs to determine differences in immunogenicity. Antibody titers against the corresponding immunogen were defined as the reciprocal of the highest dilution with absorbance ≧0.2. Each bar represents an individual mouse. Designation on the x-axis represents time at which sera was sampled, e.g. 1y+3 corresponds to serum collected three weeks after the first immunization. Neu-N mice have an FVB/n background and express normal rat neu proto-oncogene under control of a mammary-specific promoter. These mice show tolerance to neu relative to non-transgenic mice (Cancer Research 60, 3569). B demonstrates that although these mice are tolerant to rat neu they are able to generate an immune response against the peptide immunogens.
Figure 14:
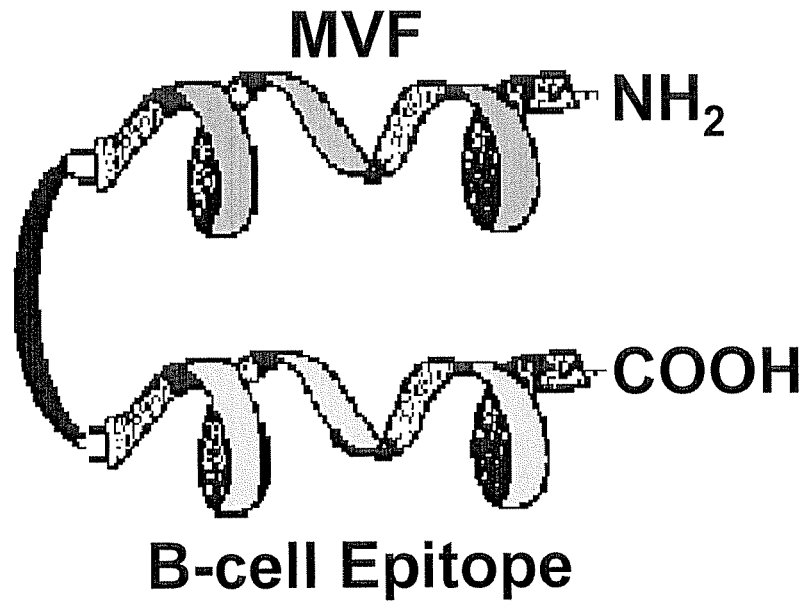
FIG. 14 shows a schematic representation of the chimeric peptide vaccine construct consisting of the 'promiscuous' Th-cell epitope MVF co-linearly synthesized with the B-cell epitope via a flexible linker (GPSL,) (SEQ ID NO: 18), allowing independent folding of MVF and the B-cell epitope. This combination may help to elicit optimal antibody production by activation of both the humoral and innate arms of the immune system.
Figure 15:
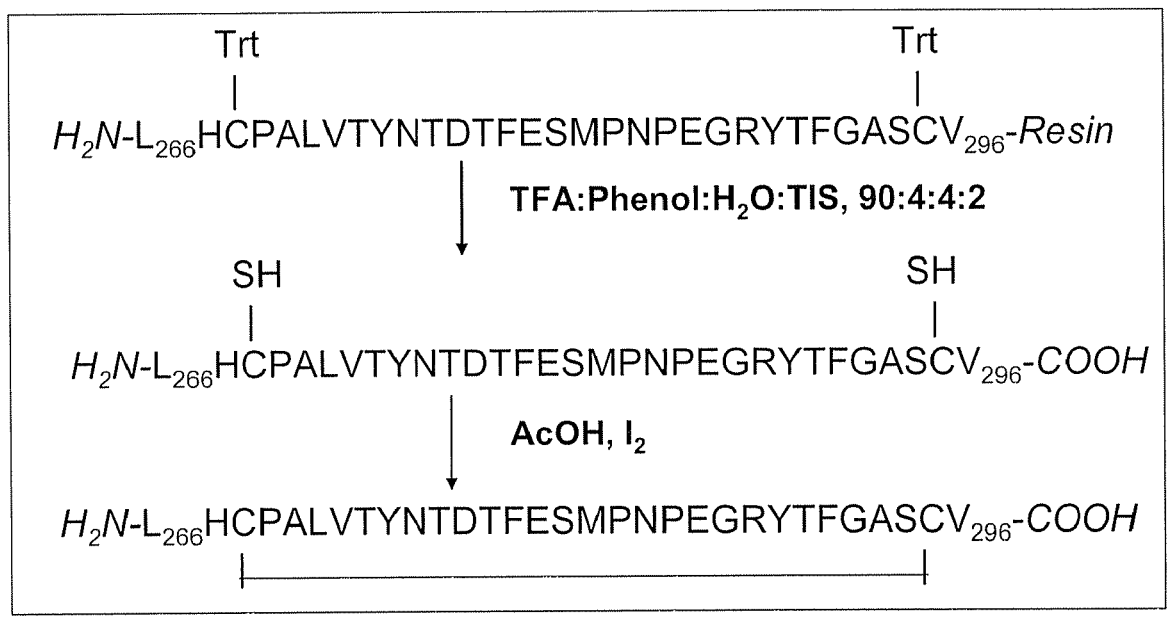
FIG. 15 shows that iodine oxidation was used to form the naturally occurring disulfide bond between Cys268 and Cys295 (SEQ ID NO: 28)
Figure 16:
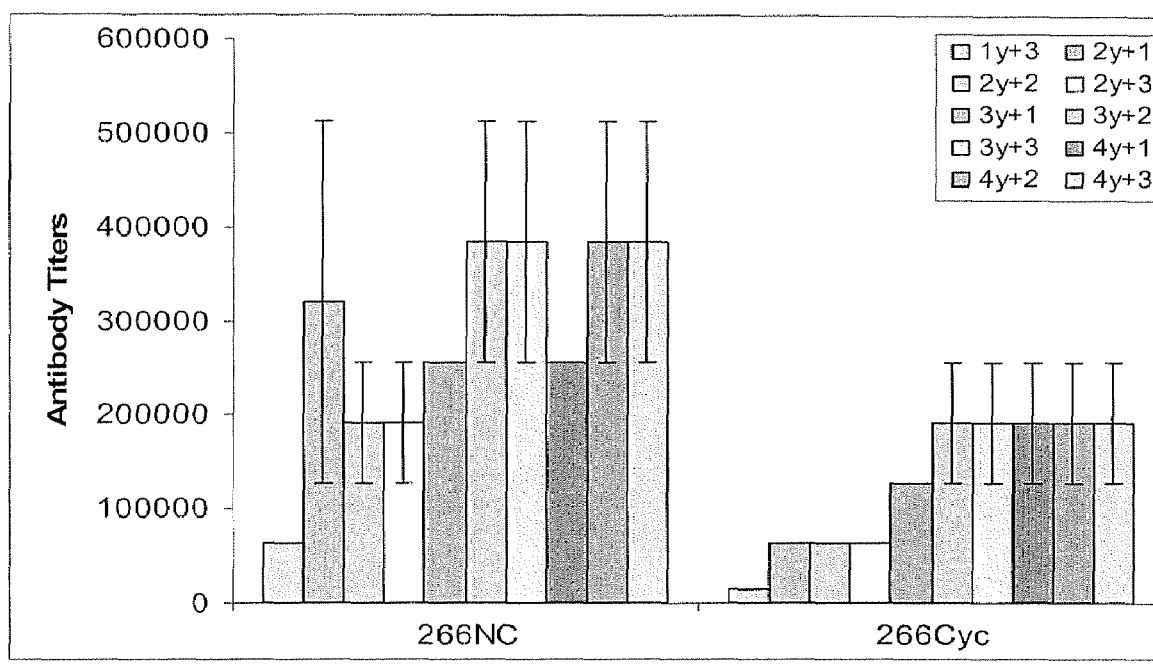
FIG. 16 shows the immunogenicity in NZW rabbits immunized with MVFHER2(266-296) non-cyclized (NC) and cyclized (CYC) peptides. Serum is collected weekly and antibodies purified for use in diagnostic studies. Antibody titers are determined by direct ELISA.
Figure 17:
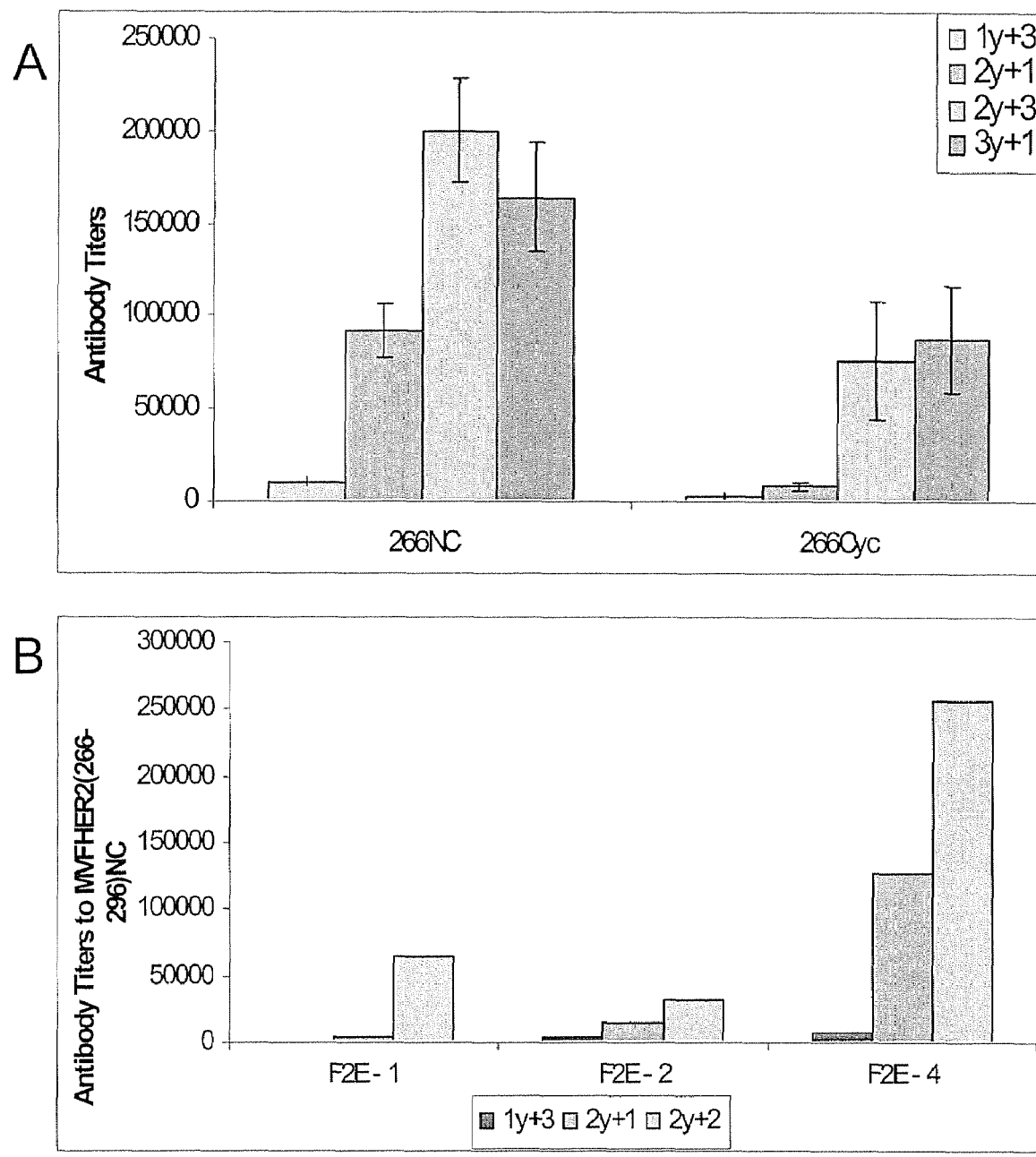
FIG. 17 shows A) immunogenicity in WT FVB/n mice immunized with either MVFHER2(266-296) cyclized (CYC) or non-cyclized (NC) peptide (8 mice/group). B) immunogenicity in 3 Neu over-expressing mice with FVB/n background. Antibody titers are determined by direct ELISA.
Figure 18:
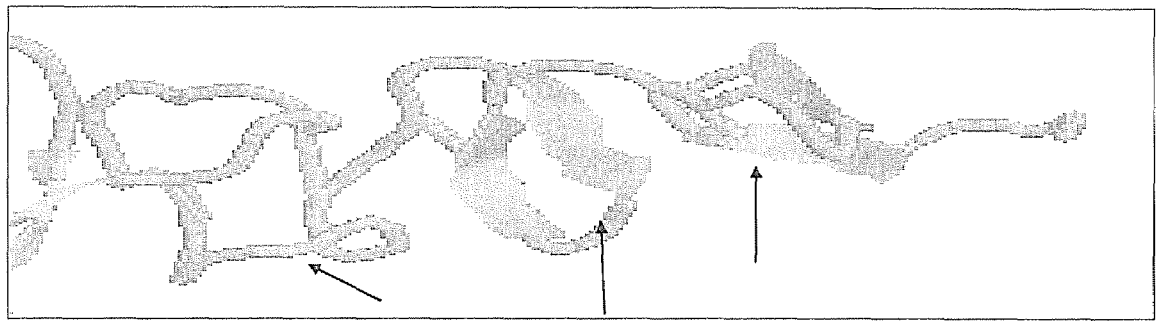
FIG. 18 shows the ribbon structure of the extracellular domain of HER-2 that interacts with herceptin. The arrows show the three loops where HER-2 makes contact with herceptin.
Figure 19:
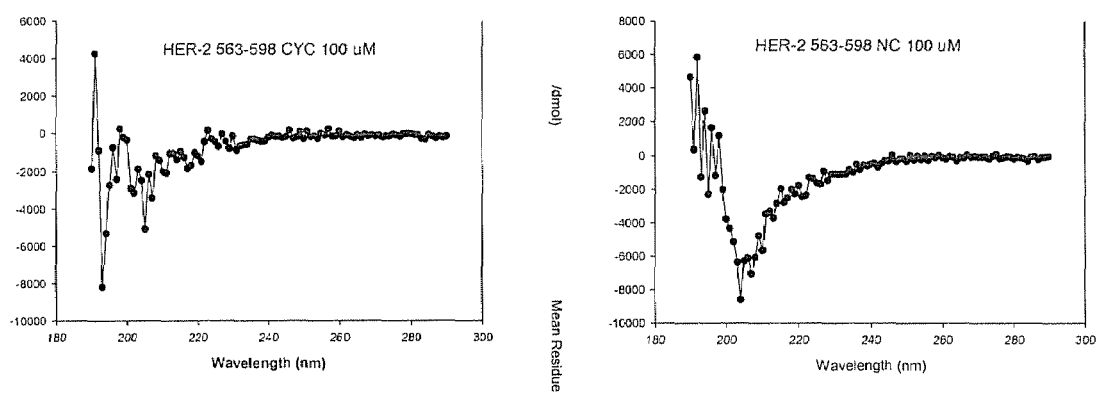
FIG. 19 shows the CD spectroscopy measurements that were performed using 100 uM solution of Her-2 563-598 CYC and Her-2 563-598 NC in water. Epitope HER-2 563-598 CYC, which is constrained with three disulfide bonds shows CD ellipticity minima at 193 nm, while epitope HER-2 563-598 NC free peptide shows CD ellipticity minima at 204 nm, which demonstrate significant differences in secondary structure.
Figure 20:
FIG. 20 shows the HER-2 563-598 epitope (SEQ ID NO: 29), and strategy for selective oxidation, reduction and disulfide bond analysis using a biotinylation agent, which attacks free sulfhydryl groups and therefore can be used to determine the completion of disulfide pairing.
Figure 21:
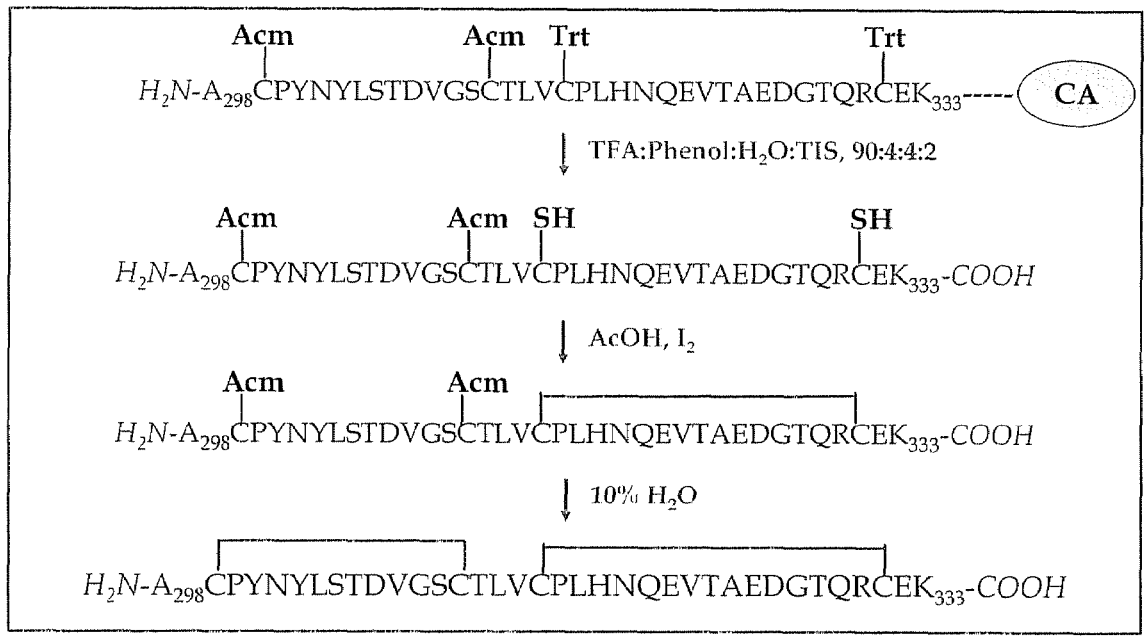
FIG. 21 shows the regioselective disulfide formation. Side chain protection for residues 315 and 331 was trityl, which was conveniently removed upon cleavage from the resin. The side chain of cysteine residues at 299 and 311 was protected with Acm, which can be selectively removed and cyclized by oxidation (I2) after the first cyclization (SEQ ID NO: 30)
Figure 22:
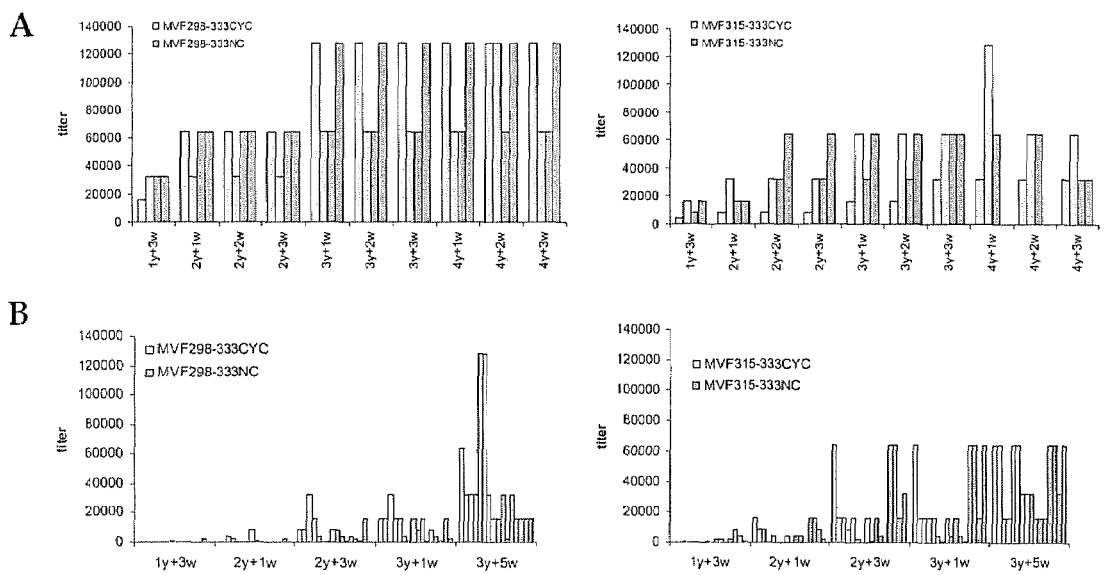
FIG. 22 shows the antibody response against peptides in out bred NZW rabbits (A) and inbred FVB/n mice (B). Direct ELISAs were performed on sera from animals immunized with the cyclized (CYC) and linear (NC) constructs to determine differences in immunogenicity. Antibody titers against the corresponding immunogen were defined as the reciprocal of the highest dilution with absorbance ≧0.2. Each bar represents an individual animal. Designation on the x-axis represents time at which sera was sampled, e.g. 1y+3w corresponds to serum collected three weeks after the first immunization.
Figure 23:
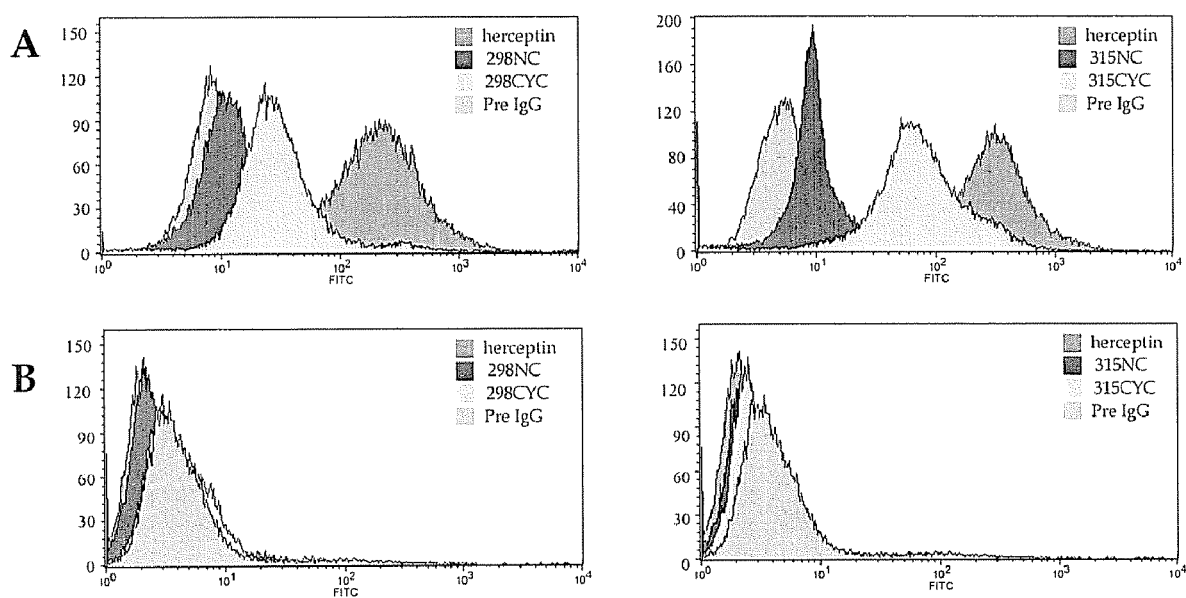
FIG. 23 shows the cross-reactivity of peptide antibodies to HER-2. The reactivity of purified antibodies from immunized rabbit sera was tested with (A) BT474 (HER-2high) and (B) MDA468 (HER-2low) breast cancer cell lines using flow cytometric analysis. Ab binding was detected with goat-anti rabbit FITC-conjugated abs. The x-axis represents fluorescent intensity, and the y-axis represents relative cell number. Each histogram contains an overlay of rabbit pre IgG, peptide antibodies, and herceptin, a human mAb that binds HER-2.
Figure 24:
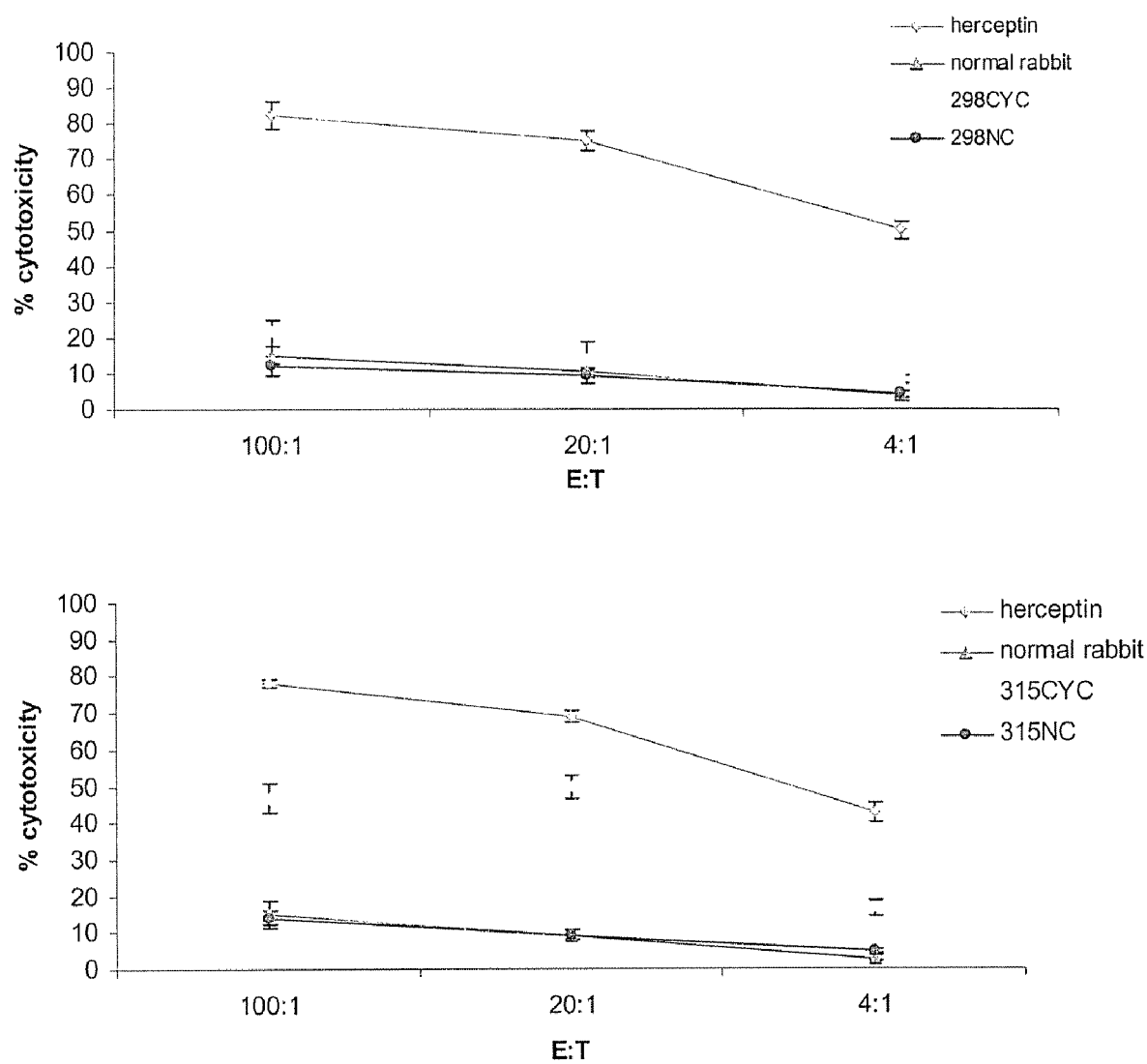
FIG. 24 shows that peptide antibodies induce ADCC (antibody dependent cell-mediated cytotoxicity) against BT474 breast cancer cells in vitro. Target cell line BT474 was incubated with peptide antibodies from rabbits, normal rabbit IgG, or herceptin in the presence of Na51 CrO4 for one hour. After three washings target cells were cultured with human PBMC effector cells to give an effector:target (E:T) ratio of 100:1, 20:1, and 4:1 for four hours at 37° C. Supernatant was subsequently harvested and radioactivity determined using a γ-counter. Cytotoxicity was calculated from the formula 100× (A-B)/(C-B) where A represents 51Cr (cpm) from test supernatant, B represents 51Cr (cpm) from target alone in culture (spontaneous), and C represents maximum 51Cr release from cells lysed with 5% SDS. Results represent the average (±SEM) of triplicate samples.
Figure 25:
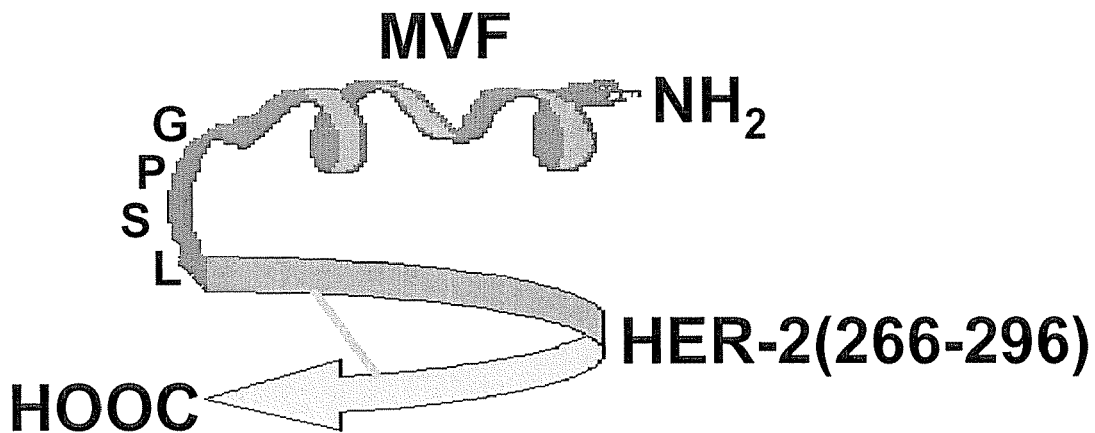
FIG. 25 shows a schematic representation of the chimeric peptide vaccine construct consisting of the 'promiscuous' TH-cell epitope derived from the measles virus fusion protein (MVF, residues 288-302) co-linearly synthesized with the B-cell epitope (HER-2(266-296)) via a flexible linker (GPSL) (SEQ ID NO: 18), allowing independent folding of MVF and the B-cell epitope.
Figure 26:
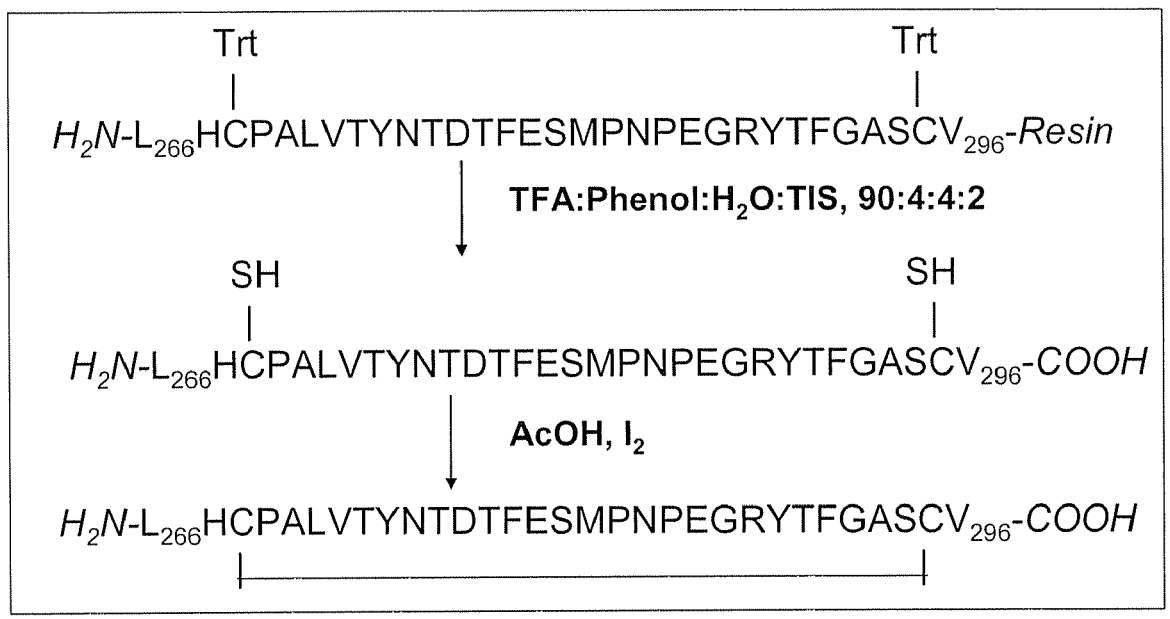
FIG. 26 shows solid-phase peptide synthesis was performed using preloaded Fmoc-Val-CLEAR Acid resin. Peptides were cleaved using Reagent B (TFA:Phenol:H2O:TIS, 90:4:4:1) and crude peptide purifed by RP-HPLC. Iodine oxidation was used to form the naturally occurring disulfide bond between Cys268 and Cys295 (SEQ ID NO: 28)
Figure 27:
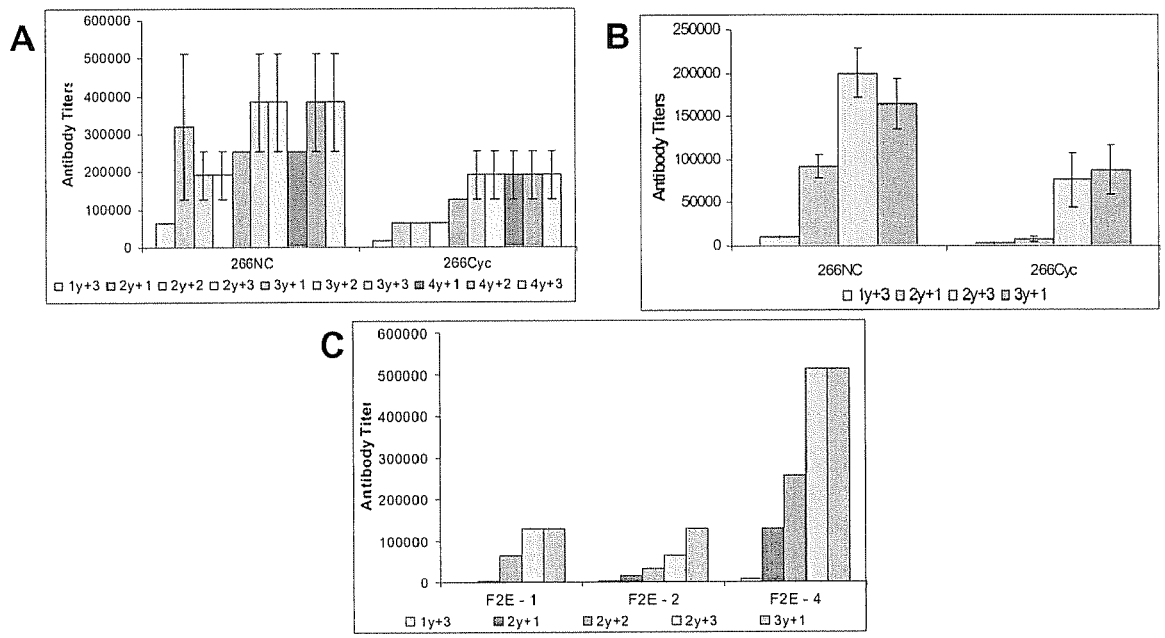
FIG. 27 shows A) Antibody titers of NZW rabbits mice immunized with MVF-HER-2(266-296) noncyclized and cyclized peptides. B) Antibody titers of wild-type FVB/n mice immunized with MVF-HER-2(266-296) noncyclized and cyclized peptides. C) Antibody titers of Neu overexpressing FVB/n mice immunized with MVF-HER-2(266-296). Serum was collected weekly and titers determined by direct ELISA.
Figure 28:
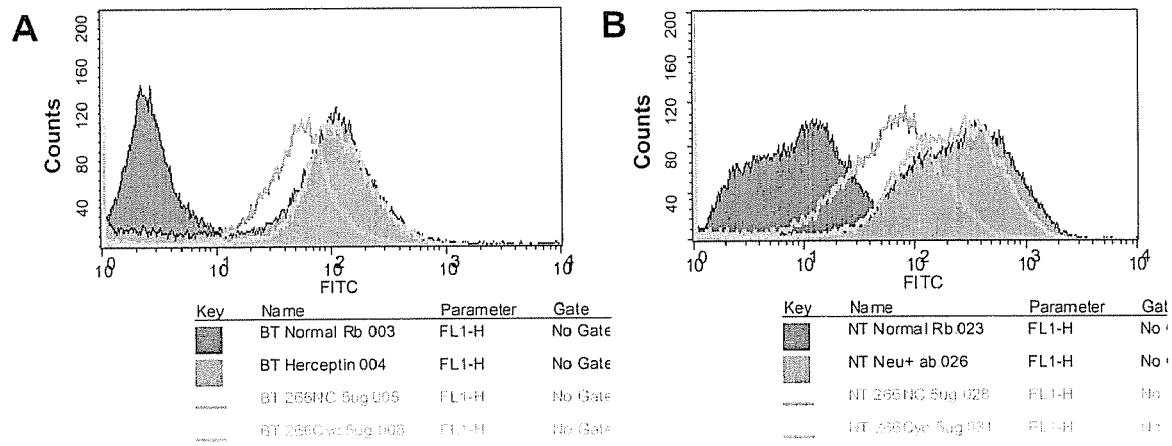
FIG. 28 shows the purified MVF-HER-2(266-296) cyclized and noncyclized antibodies tested for their ability to bind to the native protein on human BT474 HER-2 overexpressing tumor cells (A) and mouse NT2.5 neu-overexpressing tumor cells (B). Both antibodies were shifted compared to the normal IgG isotype control and had similar binding compared to the positive controls (Herceptin for BT474 and anti-c-ErbB2/c-Neu (Ab-4) for NT2.5)
Figure 29:
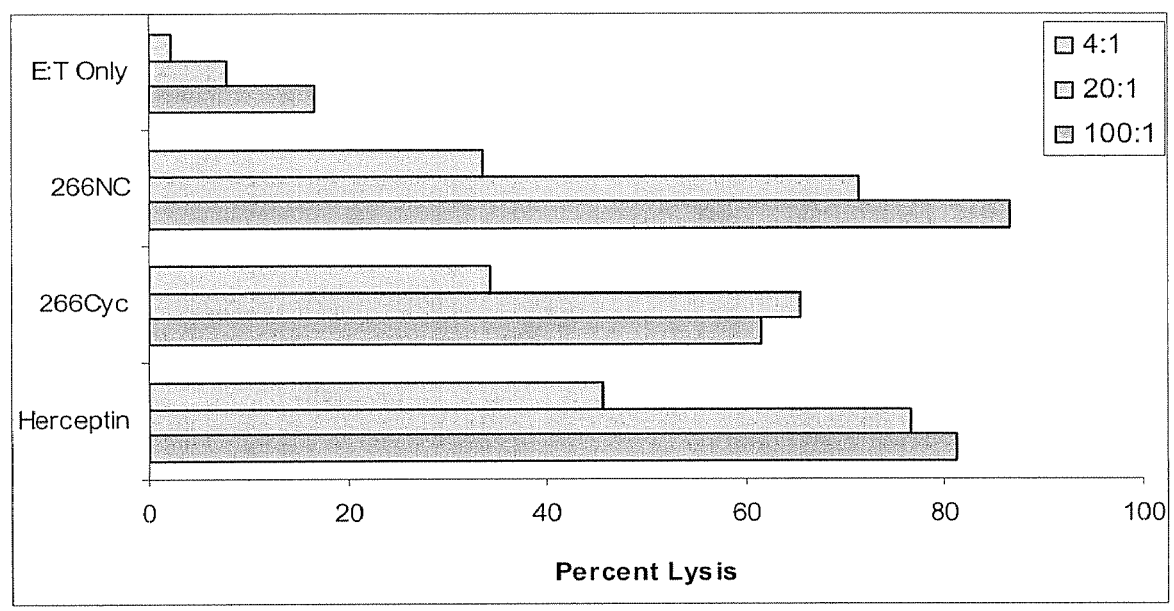
FIG. 29 shows antibody-dependent cell-mediated cytotoxicity determined by incubating BT474 cells with purified MVF-HER-2(266-296) cyclized and noncyclized antibodies and 51Cr, then exposing the antibody-bound cells to human PBMCs, which perform immunologic lysis on the BT474 cells.

To determine if antibodies elicited by the Herceptin-peptide epitopes show differences in their ability to recognize the HER-2 receptor, the binding of FVB/n purified antibodies to the HER-2 over-expressing human breast cancer cell line BT474 was tested. FIG. 5 C, D shows that both the 597-626 and the 613-626 construct are shifted relative to normal mouse antibodies. However the 563-598 and the 585-598 constructs showed little shift compared to normal mouse antibodies (FIG. 5 A, B). The 563-598 contains two of the three contacts that HER-2 makes with trastuzumab. The 597-626 epitope, which contains the last contact point with trastuzumab consist of 11 amino acids that recognize the native protein (FIG. 5C). The shorter version of this sequence 613-626 also recognizes the native protein in a similar manner (FIG. 5D). A plausible explanation for the lack of recognition of epitope 563-598 and 585-598 is that there is a potential glycosylation site at residues 571-573 (NGS) with the large bulky sugar moiety interfering sterically and prevents binding of that epitope.

Example 6

Tumor Challenge

To better understand the potential clinical benefit associated with introducing conformational constraints into B-cell epitope vaccines, both FVB/n and neu-N transgenic mice were challenged with the tumor cell line NT2.5 derived from a spontaneous mammary tumor isolated from a neu-N transgenic mouse. As a consequence of net over-expression these mice develop spontaneous mammary adenocarcinomas in a maimer similar to that observed in human breast cancer patients, and are therefore a suitable model for human breast cancer studies. Groups of FVB/n mice were challenged with $5\times10^6$ NT2.5 cells s.c. (lower abdomen) two weeks after final immunization. Tumor measurements were taken twice weekly until day 55. Tumor volumes were calculated by the formula (long measurement×short measurement $^2$)/2. Note that after day 30 the tumors in FVB/n mice begin to regress, indicative of rejection of the tumor. With subsequent tumor studies using FVB/n mice, tumors were measured to day 30. Mice immunized with the 563-598 NC and SS constructs had mean tumor volumes at day 30 of 166.517 and 173.7292 $mm^3$ respectively while unimmunized mice had a mean tumor volume of 346.6563 $mm^3$ (data not shown). By day 33 mice immunized with the 613-626 and 585-598CYC showed a reduction in tumor volume compared to both unimmunized and MVF immunized mice. While there appears to be some moderate success in terms of reduction in tumor burden of mice immunized with the trastuzumab B-cell epitopes, nearly all mice developed tumors.

Example 7

Design and Evaluation of Novel Pertuzumab-Binding Conformational B-Cell Epitopes The 3 peptide sequence listed in the Table 2 were designed to further delineate the minimal sequence to elicit an antibody similar to the pertuzumab binding site. These complex conformational peptide epitopes have been synthesized, successfully purified, and cyclized with the correct disulfide pairings. Epitope 266-296 (SH bond between Cys268-Cys295, Epitope 298-333 (SH bond between Cys 299-Cys311, and Epitope 315-333 (SH bond Cys 315-Cys 331) should allow us to delineate the minimal pertuzumab binding epitope.

TABLE 2 shows engineered HER-2 B chimeric peptides
(SEQ ID NOS 23-25 are disclosed respectively in order of appearance).

| Designation | Peptide | Sequence |
| --- | --- | --- |
| MVF 266 CYC | 266-296 | H2N-*KLLSLIKGVIVHRLEGVE*-GPSL-LH☐PA LVTYNTDTFESMPNPEGRYTFGAS☐V-COOH |
| MVF 298 CYC | 298-333 | H2N-*KLLSLIKGVIVHRLEGVE*-GPSL-A☐PYNYLSTDVGS☐TLV☐PLHNQEVTAEDGTQR☐EK-COOH |
| MVF 315 CYC | 315-333 | H2N-*KLLSLIKGVIVHRLEGVE*-GPSL-CPLHNQEVTAEDGTQRCEK-COOH |

Additional results are shown in FIGS. 6-30.

It will be obvious to those skilled in the art that various changes may be made without departing from the scope of the invention, which is not to be considered limited to what is described in the specification.

---

What is claimed is:

1. An immunogenic composition comprising a chimeric peptide, wherein the chimeric peptide comprises a HER-2 B epitope, a T helper (Th) epitope, and a linker joining the HER-2 B epitope to the Th epitope, wherein:
   the HER-2 B epitope consists of LHCPALVTYNTDT-FESMPNPEGRYTFGASCV (SEQ ID NO: 6);
   the Th epitope comprises KLLSLIKGVIVHRLEGVE (SEQ ID NO: 10); and
   the linker is of from 1 to 15 amino acids.

2. The composition as claimed in claim 1 wherein at least one of the HER-2 B epitope, the Th epitope, or the linker is in retro-inverso form.

3. The composition as claimed in claim 1 wherein the linker comprises 2 to 15 amino acids.

4. The composition as claimed in claim 1 wherein the linker comprises GPSL (SEQ ID NO: 18).

5. The composition as claimed in claim 1 wherein the Th epitope has a sequence of NSVDDALINSTIYSYFPSV (SEQ ID NO: 11).

6. The composition as claimed in claim 1 wherein the Th epitope has a sequence of PGINGKAIHLVNNQSSE (SEQ ID NO: 12).

7. The composition as claimed in claim 1 wherein the Th epitope has a sequence of QYIKANSKFIGITEL (SEQ ID NO: 13).

8. The composition as claimed in claim 1 wherein the Th epitope has a sequence of FNNFTVSFWLRVPKVSASHLE (SEQ ID NO: 14).

9. The composition as claimed in claim 1 wherein the Th epitope has a sequence of LSEIKGVIVHRLEGV (SEQ ID NO: 15).

10. The composition as claimed in claim 1 wherein the Th epitope has a sequence of FFLLTRILTIPQSLN (SEQ ID NO: 16).

11. The composition as claimed in claim 1 wherein the Th epitope has a sequence of TCGVGVRVRSRVNAANKKPE (SEQ ID NO: 17).

12. A method of stimulating an immune response in a subject comprising administering to said subject the composition of claim 1.

* * * * *

SEQUENCE LISTING

<160> NUMBER OF SEQ ID NOS: 30

<210> SEQ ID NO 1
<211> LENGTH: 1255
<212> TYPE: PRT
<213> ORGANISM: Homo sapiens

<400> SEQUENCE: 1

```
Met Glu Leu Ala Ala Leu Cys Arg Trp Gly Leu Leu Ala Leu Leu
 1               5                  10                  15

Pro Pro Gly Ala Ala Ser Thr Gln Val Cys Thr Gly Thr Asp Met Lys
                 20                  25                  30

Leu Arg Leu Pro Ala Ser Pro Glu Thr His Leu Asp Met Leu Arg His
             35                  40                  45

Leu Tyr Gln Gly Cys Gln Val Val Gln Gly Asn Leu Glu Leu Thr Tyr
         50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
```

-continued

```
            210                 215                 220
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
                290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
                370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
                450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
                530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
                610                 615                 620

Pro Cys Pro Ile Asn Cys Thr His Ser Cys Val Asp Leu Asp Asp Lys
625                 630                 635                 640
```

-continued

```
Gly Cys Pro Ala Glu Gln Arg Ala Ser Pro Leu Thr Ser Ile Val Ser
                645                 650                 655

Ala Val Val Gly Ile Leu Leu Val Val Leu Gly Val Val Phe Gly
        660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055
```

```
Gly Asp Leu Thr Leu Gly Leu Glu Pro Ser Glu Glu Ala Pro Arg
        1060                1065                1070

Ser Pro Leu Ala Pro Ser Glu Gly Ala Gly Ser Asp Val Phe Asp Gly
    1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
        1125                1130                1135

Pro Glu Tyr Val Asn Gln Pro Asp Val Arg Pro Gln Pro Pro Ser Pro
        1140                1145                1150

Arg Glu Gly Pro Leu Pro Ala Ala Arg Pro Ala Gly Ala Thr Leu Glu
        1155                1160                1165

Arg Ala Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
        1205                1210                1215

Phe Asp Asn Leu Tyr Tyr Trp Asp Gln Asp Pro Pro Glu Arg Gly Ala
        1220                1225                1230

Pro Pro Ser Thr Phe Lys Gly Thr Pro Thr Ala Glu Asn Pro Glu Tyr
        1235                1240                1245

Leu Gly Leu Asp Val Pro Val
        1250                1255

<210> SEQ ID NO 2
<211> LENGTH: 36
<212> TYPE: PRT
<213> ORGANISM: Homo sapiens

<400> SEQUENCE: 2

Cys His Pro Glu Cys Gln Pro Gln Asn Gly Ser Val Thr Cys Phe Gly
1               5                   10                  15

Pro Glu Ala Asp Gln Cys Val Ala Cys Ala His Tyr Lys Asp Pro Pro
            20                  25                  30

Phe Cys Val Ala
        35

<210> SEQ ID NO 3
<211> LENGTH: 14
<212> TYPE: PRT
<213> ORGANISM: Homo sapiens

<400> SEQUENCE: 3

Val Ala Cys Ala His Tyr Lys Asp Pro Pro Phe Cys Val Ala
1               5                   10

<210> SEQ ID NO 4
<211> LENGTH: 30
<212> TYPE: PRT
<213> ORGANISM: Homo sapiens

<400> SEQUENCE: 4

Val Ala Arg Cys Pro Ser Gly Val Lys Pro Asp Leu Ser Tyr Met Pro
1               5                   10                  15

Ile Trp Lys Phe Pro Asp Glu Glu Gly Ala Cys Gln Pro Leu
```

```
                       20                  25                  30

<210> SEQ ID NO 5
<211> LENGTH: 14
<212> TYPE: PRT
<213> ORGANISM: Homo sapiens

<400> SEQUENCE: 5

Ile Trp Lys Phe Pro Asp Glu Glu Gly Ala Cys Gln Pro Leu
 1               5                  10

<210> SEQ ID NO 6
<211> LENGTH: 31
<212> TYPE: PRT
<213> ORGANISM: Homo sapiens

<400> SEQUENCE: 6

Leu His Cys Pro Ala Leu Val Thr Tyr Asn Thr Asp Thr Phe Glu Ser
 1               5                  10                  15

Met Pro Asn Pro Glu Gly Arg Tyr Thr Phe Gly Ala Ser Cys Val
                20                  25                  30

<210> SEQ ID NO 7
<211> LENGTH: 36
<212> TYPE: PRT
<213> ORGANISM: Homo sapiens

<400> SEQUENCE: 7

Ala Cys Pro Tyr Asn Tyr Leu Ser Thr Asp Val Gly Ser Cys Thr Leu
 1               5                  10                  15

Val Cys Pro Leu His Asn Gln Glu Val Thr Ala Glu Asp Gly Thr Gln
                20                  25                  30

Arg Cys Glu Lys
             35

<210> SEQ ID NO 8
<211> LENGTH: 19
<212> TYPE: PRT
<213> ORGANISM: Homo sapiens

<400> SEQUENCE: 8

Cys Pro Leu His Asn Gln Glu Val Thr Ala Glu Asp Gly Thr Gln Arg
 1               5                  10                  15

Cys Glu Lys

<210> SEQ ID NO 9
<211> LENGTH: 24
<212> TYPE: PRT
<213> ORGANISM: Homo sapiens

<400> SEQUENCE: 9

Cys Pro Ile Asn Cys Thr His Ser Cys Val Asp Leu Asp Asp Lys Gly
 1               5                  10                  15

Cys Pro Ala Glu Gln Arg Ala Ser
                20

<210> SEQ ID NO 10
<211> LENGTH: 18
<212> TYPE: PRT
<213> ORGANISM: Homo sapiens

<400> SEQUENCE: 10
```

Lys Leu Leu Ser Leu Ile Lys Gly Val Ile Val His Arg Leu Glu Gly
 1               5                  10                 15

Val Glu

<210> SEQ ID NO 11
<211> LENGTH: 19
<212> TYPE: PRT
<213> ORGANISM: Homo sapiens

<400> SEQUENCE: 11

Asn Ser Val Asp Asp Ala Leu Ile Asn Ser Thr Ile Tyr Ser Tyr Phe
 1               5                  10                 15

Pro Ser Val

<210> SEQ ID NO 12
<211> LENGTH: 17
<212> TYPE: PRT
<213> ORGANISM: Homo sapiens

<400> SEQUENCE: 12

Pro Gly Ile Asn Gly Lys Ala Ile His Leu Val Asn Asn Gln Ser Ser
 1               5                  10                 15

Glu

<210> SEQ ID NO 13
<211> LENGTH: 15
<212> TYPE: PRT
<213> ORGANISM: Homo sapiens

<400> SEQUENCE: 13

Gln Tyr Ile Lys Ala Asn Ser Lys Phe Ile Gly Ile Thr Glu Leu
 1               5                  10                 15

<210> SEQ ID NO 14
<211> LENGTH: 21
<212> TYPE: PRT
<213> ORGANISM: Homo sapiens

<400> SEQUENCE: 14

Phe Asn Asn Phe Thr Val Ser Phe Trp Leu Arg Val Pro Lys Val Ser
 1               5                  10                 15

Ala Ser His Leu Glu
            20

<210> SEQ ID NO 15
<211> LENGTH: 15
<212> TYPE: PRT
<213> ORGANISM: Homo sapiens

<400> SEQUENCE: 15

Leu Ser Glu Ile Lys Gly Val Ile Val His Arg Leu Glu Gly Val
 1               5                  10                 15

<210> SEQ ID NO 16
<211> LENGTH: 15
<212> TYPE: PRT
<213> ORGANISM: Homo sapiens

<400> SEQUENCE: 16

Phe Phe Leu Leu Thr Arg Ile Leu Thr Ile Pro Gln Ser Leu Asn
 1               5                  10                 15

```
<210> SEQ ID NO 17
<211> LENGTH: 20
<212> TYPE: PRT
<213> ORGANISM: Homo sapiens

<400> SEQUENCE: 17

Thr Cys Gly Val Gly Val Arg Val Arg Ser Arg Val Asn Ala Ala Asn
 1               5                  10                  15

Lys Lys Pro Glu
            20

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 18

Gly Pro Ser Leu
 1

<210> SEQ ID NO 19
<211> LENGTH: 58
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 19

Lys Leu Leu Ser Leu Ile Lys Gly Val Ile Val His Arg Leu Glu Gly
 1               5                  10                  15

Val Glu Gly Pro Ser Leu Cys His Pro Glu Cys Gln Pro Gln Asn Gly
                20                  25                  30

Ser Val Thr Cys Phe Gly Pro Glu Ala Asp Gln Cys Val Ala Cys Ala
            35                  40                  45

His Tyr Lys Asp Pro Pro Phe Cys Val Ala
        50                  55

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 20

Lys Leu Leu Ser Leu Ile Lys Gly Val Ile Val His Arg Leu Glu Gly
 1               5                  10                  15

Val Glu Gly Pro Ser Leu Val Ala Cys Ala His Tyr Lys Asp Pro Pro
                20                  25                  30

Phe Cys Val Ala
            35

<210> SEQ ID NO 21
<211> LENGTH: 52
<212> TYPE: PRT
<213> ORGANISM: Artificial Sequence
<220> FEATURE:
<223> OTHER INFORMATION: Description of Artificial Sequence: Synthetic
      chimeric peptide
```

```
<400> SEQUENCE: 21

Lys Leu Leu Ser Leu Ile Lys Gly Val Ile Val His Arg Leu Glu Gly
  1               5                  10                  15

Val Glu Gly Pro Ser Leu Val Ala Arg Cys Pro Ser Gly Val Lys Pro
             20                  25                  30

Asp Leu Ser Tyr Met Pro Ile Trp Lys Phe Pro Asp Glu Glu Gly Ala
         35                  40                  45

Cys Gln Pro Leu
     50

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 22

Lys Leu Leu Ser Leu Ile Lys Gly Val Ile Val His Arg Leu Glu Gly
  1               5                  10                  15

Val Glu Gly Pro Ser Leu Ile Trp Lys Phe Pro Asp Glu Glu Gly Ala
             20                  25                  30

Cys Gln Pro Leu
         35

<210> SEQ ID NO 23
<211> LENGTH: 53
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 23

Lys Leu Leu Ser Leu Ile Lys Gly Val Ile Val His Arg Leu Glu Gly
  1               5                  10                  15

Val Glu Gly Pro Ser Leu Leu His Cys Pro Ala Leu Val Thr Tyr Asn
             20                  25                  30

Thr Asp Thr Phe Glu Ser Met Pro Asn Pro Glu Gly Arg Tyr Thr Phe
         35                  40                  45

Gly Ala Ser Cys Val
     50

<210> SEQ ID NO 24
<211> LENGTH: 58
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 24

Lys Leu Leu Ser Leu Ile Lys Gly Val Ile Val His Arg Leu Glu Gly
  1               5                  10                  15

Val Glu Gly Pro Ser Leu Ala Cys Pro Tyr Asn Tyr Leu Ser Thr Asp
             20                  25                  30

Val Gly Ser Cys Thr Leu Val Cys Pro Leu His Asn Gln Glu Val Thr
         35                  40                  45

Ala Glu Asp Gly Thr Gln Arg Cys Glu Lys
     50                  55
```

<210> SEQ ID NO 25
<211> LENGTH: 41
<212> TYPE: PRT
<213> ORGANISM: Artificial Sequence
<220> FEATURE:
<223> OTHER INFORMATION: Description of Artificial Sequence: Synthetic chimeric peptide

<400> SEQUENCE: 25

```
Lys Leu Leu Ser Leu Ile Lys Gly Val Ile Val His Arg Leu Glu Gly
 1               5                  10                  15

Val Glu Gly Pro Ser Leu Cys Pro Leu His Asn Gln Glu Val Thr Ala
            20                  25                  30

Glu Asp Gly Thr Gln Arg Cys Glu Lys
        35                  40
```

<210> SEQ ID NO 26
<211> LENGTH: 46
<212> TYPE: PRT
<213> ORGANISM: Artificial Sequence
<220> FEATURE:
<223> OTHER INFORMATION: Description of Artificial Sequence: Synthetic chimeric peptide

<400> SEQUENCE: 26

```
Lys Leu Leu Ser Leu Ile Lys Gly Val Ile Val His Arg Leu Glu Gly
 1               5                  10                  15

Val Glu Gly Pro Ser Leu Cys Pro Ile Asn Cys Thr His Ser Cys Val
            20                  25                  30

Asp Leu Asp Asp Lys Gly Cys Pro Ala Glu Gln Arg Ala Ser
        35                  40                  45
```

<210> SEQ ID NO 27
<211> LENGTH: 35
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

```
His Pro Glu Cys Gln Pro Gln Asn Gly Ser Val Thr Cys Phe Gly Pro
 1               5                  10                  15

Glu Ala Asp Gln Cys Val Ala Cys Ala His Tyr Lys Asp Pro Pro Phe
            20                  25                  30

Cys Val Ala
        35
```

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

```
His Cys Pro Ala Leu Val Thr Tyr Asn Thr Asp Thr Phe Glu Ser Met
 1               5                  10                  15

Pro Asn Pro Glu Gly Arg Tyr Thr Phe Gly Ala Ser Cys Val
            20                  25                  30
```

```
<210> SEQ ID NO 29
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys His Pro Glu Cys Gln Pro Gln Asn Gly Ser Val Thr Cys Phe Gly
 1               5                  10                  15

Pro Glu Ala Asp Gln Cys Val Ala Cys Ala His Tyr Lys Asp Pro Pro
            20                  25                  30

Phe Cys Val Ala
        35

<210> SEQ ID NO 30
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Pro Tyr Asn Tyr Leu Ser Thr Asp Val Gly Ser Cys Thr Leu Val
 1               5                  10                  15

Cys Pro Leu His Asn Gln Glu Val Thr Ala Glu Asp Gly Thr Gln Arg
            20                  25                  30

Cys Glu Lys
        35
```